United States Patent
Shan et al.

(10) Patent No.: US 11,920,142 B2
(45) Date of Patent: Mar. 5, 2024

(54) **NEGATIVE REGULATOR AtRTP5 AND USE THEREOF IN PLANT RESISTANCE TO *PHYTOPHTHORA***

(71) Applicant: Northwest A&F University, Shaanxi (CN)

(72) Inventors: Weixing Shan, Shaanxi (CN); Weiwei Li, Shaanxi (CN)

(73) Assignee: Northwest A&F University, Shaanxi (CN)

( * ) Notice: Subject to any disclaimer, the term of this patent is extended or adjusted under 35 U.S.C. 154(b) by 0 days.

(21) Appl. No.: 17/019,197

(22) Filed: Sep. 12, 2020

(65) Prior Publication Data

US 2021/0095307 A1    Apr. 1, 2021

(30) Foreign Application Priority Data

Sep. 27, 2019   (CN) .......................... 201910922156.8

(51) Int. Cl.
*C12N 15/82* (2006.01)
*C07K 14/415* (2006.01)

(52) U.S. Cl.
CPC ........ *C12N 15/8282* (2013.01); *C07K 14/415* (2013.01)

(58) Field of Classification Search
None
See application file for complete search history.

(56) References Cited

U.S. PATENT DOCUMENTS

| | | | | |
|---|---|---|---|---|
| 2002/0007501 A1* | 1/2002 | Song et al. | ........ | C12N 15/8271 800/290 |
| 2009/0094717 A1* | 4/2009 | Troukhan et al. | ... | C07K 14/415 536/23.6 |

OTHER PUBLICATIONS

Reynolds et al. (2004) Nature Biotech 22(3):326-30.*
Thomas et al. (2001) Plant J 25:417-25.*
Klahre et al. (2002) Proc Natl Acad Sci 99:11981-86.*
Rost (1999) Prot Engin 12(2):85-94.*
Whisstock & Lesk (2003) Q Rev Biophys. 36(3):307-40.*
Pan et al. (2016) New Phytologist 209:1641-54.*
Li et al (2020) Plant Physiol 21(1):95-108.*
Burch-Smith et al. (2004) "Applications and advantages of virus-induced gene silencing for gene function studies in plants," Plant J 39:734-46.*
Lu et al. (2003) "Virus-induced gene silencing in plants," Meth 30(4):296-303.*
Martínez de Alba et al. (2013) "Gene silencing in plants: a diversity of pathways," Biochim Biophys Acta 1829:1300-08.*
Reynolds et al. (2004) "Rational siRNA design for RNA interference," Nature Biotech 22(3):326-30.*
Thomas et al. (2001) "Size constraints for targeting post-transcriptional gene silencing and for RNA-directed methylation in Nicotiana benthamiana using a potato virus X vector," Plant J 25:417-25.*
Klahre et al. (2002) "High molecular weight RNAs and small interfering RNAs induce systemic posttranscriptional gene silencing in plants," Proc Natl Acad Sci 99:11981-86.*

* cited by examiner

*Primary Examiner* — Russell T Boggs
(74) *Attorney, Agent, or Firm* — Hickman Becker Bingham Ledesma LLP

(57) ABSTRACT

The use of a negative regulator AtRTP5 for increasing the plant resistance to *Phytophthora* is disclosed. The AtRTP5 gene negatively regulates the plant resistance to *Phytophthora* by interfering with a plant hormone immune signaling pathway. The AtRTP5 gene has a nucleotide sequence shown as SEQ ID NO: 1 or a homologous sequence having more than 50% homology with the sequence. The use of a protein encoded by a negative regulator AtRTP5 for increasing the plant resistance to *Phytophthora* is also disclosed. The plant resistance to *Phytophthora* is enhanced by reducing the expression of the protein encoded by the AtRTP5 gene with genetic engineering. The protein has an amino acid sequence shown as SEQ ID NO: 2 or a homologous sequence having more than 50% homology with the sequence.

2 Claims, 5 Drawing Sheets
Specification includes a Sequence Listing.

```
XP_015167964.1  : MRSSMSPDNSSSAPSTS------------RSSFPSAASQNLNCKH--SNVFQLLRREVAPRTKRASKFPWGENTKCTLDSYG-LKRGVGSDARQGLISWVEAESLQHLSAK   :  97
XP_015167963.1  : MRSSMSPDNSSSAPSTS------------RSSFPSAASQNLNCKH--SNVFQLLRREVAPRTKRASKFPWGENTKCTLDSYG-LKRGVGSDARQGLISWVEAESLQHLSAK   :  97
XP_006340895.1  : MRGSLWPENSSSDSSTSNFIHVPLPFPPGWNSPSLPIEQNPNCKNRCGNVFQLLTRREVSPRAKRSSKKLWDENSKYCAHSYEKLKSQVARDPRRGLISWVEAESLRHFSAK   : 113
AtRTP5          : MTQSICSSQDQSSSPRS-----------LITFPRKSATKFHRRRG--RSVFPNMLVQREMSPKAKFVPRKRWGKSRWYTDSSCG-TNNESMKETGQSLTSWVEAESLQHLSAK : 98

XP_015167964.1  : YCSLLPPPRSTIAAAFSPDGRTLASTHGDHTVKIIDCQTGKCLKVMSGHRRTPWVFRFHPLYPEILASGSLDHEVRLMDAKTAECIGSRDFYRPIASIAFHAQGEVLAVASGH : 210
XP_015167963.1  : YCSLLPPPRSTIAAAFSPDGRTLASTHGDHTVKIIDCQTGKCLKVMSGHRRTPWVFRFHPLYPEILASGSLDHEVRLMDAKTAECIGSRDFYRPIASIAFHAQGEVLAVASGH : 210
XP_006340895.1  : YCPLGAPPRSTIAAAFSTDGRTLASTHGDHTVKIIDCQSGKCLKVLSGHKRTPWVRFHPLHSEILASGSLDHEVRLMDAKTAECIGSRDFYRFIASIAFHAQGEVLAVASGH : 226
AtRTP5          : YCPLGAPPRSTIAAAFSTDGRTLASTHGDHTVKIIDCETGNCLKVLJTGHRRTPWVRFHPHHSEIVASGSLDLEVRLMNTTESCIRSHLFYRPIASIAFHAEGELLAVASGH : 211

XP_015167964.1  : KLYIMHYNRRGEASSPAIILKTRRSLRAVHFHPHGAPFLLTAEVNDLDSSDSSITRATSP---------------ANELPIMSQPFLIWPSIARGDPRMPMQQSD         : 300
XP_015167963.1  : KLYIMHYNRRGEASSPAIILKTRRSLRAVHFHPHGAPFLLTAEVNDLDSSDSSITRATSPGNLQYPPPTVYLTDAHSTYQSASANELPIMSQPFLIWPSIARGDPRMPMQQSD : 323
XP_006340895.1  : KLIWHYNRREEASSPAIIIKTRRSLRAVHFHPHGAPYLLTAEVNDLDSSDPLMTFAFSLGNLRYPPPTVYLTDAHSTYRSASANELPIMSLPIMIWPSIARGDPRMPLQQSN   : 339
AtRTP5          : KLHWWHYNRRGEGSSPTTVLKTRRSLRAVHFHPHGAPLLLTAEVNEIDSLDSSMSRATSMGYLRYPF-------PAILFTSTESNQTSLAAENEN                   : 299

XP_015167964.1  : TDVGSDSIQQRADTSSSVRLLTYSTPSGQYELLLSPIEQSASPTQEAHTSSVRENETGNQPLVDPMETGGQPEERNNQFFPFSDPAYWELPFLQGWLIGRSQATR----SEL   : 409
XP_015167963.1  : TDVGSDSIQQRADTSSSVRLLTYSTPSGQYELLLSPIEQSASPTQEAHTSSVRENETGNQPLVDPMETGGQPEERNNQFFPFSDPAYWELPFLQGMLIGRSQATR----SEL   : 432
XP_006340895.1  : VDMGSDSTQNRADTSASVRLLTYSTPSGQYELLLSPVEPTLSPAQEAQTSSSVRDTENASNPVVDPNETUDVPTEERNMQFFPSDPAYWDLPFLQGWLIGQSQAGRRSIHSEH : 452
AtRTP5          : RTSSPPLPLATSSGPSGFNSVPGNSPS---NIFIJTRAGDRTSFAVDGMDVDEAQPVGRNGIPSQVSNRSGFFELGQIRQLFHFRDRVSWELPFLQGWRLMAQGHGVAN-PVVTP : 408

XP_015167964.1  : SGATIN------PSTYGELENPSAVPLVIS-SNSHPRSGRSGSRHRSSSRSRVIPVAGAGDGAAPVNVMHDESDSQISIGRIQSEIATSLAA----AAAAELPCTVKLRIWPYDIK : 513
XP_015167963.1  : SGATIN------PSTYGELENPSAVPLVIS-SNSHPRSGRSGSRHRSSSRSRVIPVAGAGDGAAPVNVMHDESDSQISIGRIQSEIATSLAA----AAAAELPCTVKLRIWPYDIK : 536
XP_006340895.1  : SGATNI------VSAYGEVEHPAVPSIIS-NSNHPRSGRSGSRHRSSSRAIPVAGGSDSAVPINIAHNESDSQAFMSRFQSEIATSLTA----AASEELPCTVKLRVWPYDIK       : 556
AtRTP5          : TGSSNHGISAPSSTASLEAAVALLEIPSGVNLHAVSRRGGAGEQTSQP-QFSRTGLPEGVSSRNTQHG-SDAQPVNRVQSELATSIAASAAAAAELPCTVKLRMWSHDIK       : 519

XP_015167964.1  : VPCAALDAERCRLIIPHAVLCSEMGAHFSPCGRFLAACVACILPNLDSDPGFHGHLHHDTMAAATSPFRHPVAAHQVMYELRIYSLEEETFGSVLAARAIRAAHCLTSIQFSP : 626
XP_015167963.1  : VPCAALDAERCRLIIPHAVLCSEMGAHFSPCGRFLAACVACILPNLDSDPGFHGHLHHDTMAAATSPFRHPVAAHQVMYELRIYSLEEETFGSVLAARAIRAAHCLTSIQFSP : 649
XP_006340895.1  : VPCALLDAEKCRLVIPHAVLCSEMGAHFSPCGRFLAACVACIISPSMEADPGFHGQFRHD---AATSPTRHPIAAHPVMYELRIYSLEEANPGRVLASRLIRAAHCLSISQFSP : 666
AtRTP5          : DPYAQLKSDRCLFTIPHAVLCSEMGAHYSPCGRYLAACVACVFPHGEIDPGLQTQAQQDS-GLATSPTRHPVTAHQVIYELRVYSLQKESFGSVLVSRAIRAAHCLTSIQFSP : 631

XP_015167964.1  : TSEHLLAYGRRHSSLLKGSVVIDGDTTIPIYTILEVYRVSDMELVRVLPSTEDEVNVACFHFSVGGGLVYGTKEGKLRILQIDMSNCLGRTISCSPVENMLEVPTYALEG  : 736
XP_015167963.1  : TSEHLLAYGRRHSSLLKSVVIDGDTTIPIYTILEVYRVSDMELVRVLPSTEDEVNVACFHPSVGGGLVYGTKEGKLRILQIDMSNCLGRTISCSPVENMLEVPTYALEG    : 759
XP_006340895.1  : TSEHLLAYGRRHGSLLKSIVIDGDTTLPVTTILEVYRVSDMELVRVLPSAEDEVNVACFHPLVGGGLVYGTKEGKLRILQFDKSNGLDCTVSCSPDEDMLEVPTYALEG  : 776
AtRTP5          : TSEHILLAYGRRHGSLLRSIVSDGETTSHFFTVLEIYRVSDMELVRVLPSSEDEVNVACFHPSPGGGLVYGTKEGKLRIFQYNTAATSNFTGPNT--------       : 726
```

NEGATIVE REGULATOR AtRTP5 AND USE THEREOF IN PLANT RESISTANCE TO PHYTOPHTHORA

RELATED APPLICATION

This application claims priority under 35 U.S.C. 119(a)-(d) to Foreign Application No. 201910922156.8 filed in China entitled "Negative regulating factor AtRTP5 gene and application thereof to resisting plant *phytophthora* bacteria" and filed on Sep. 27, 2019, the contents of which are herein incorporated in their entirely by reference for all purposes.

REFERENCE TO AN ELECTRONIC SEQUENCE LISTING

The contents of the electronic sequence listing (60616-0011-Sequence-Listing_2023-03-01.txt; Size: 63,928 bytes; and Date of Creation: Mar. 1, 2023) is herein incorporated by reference in its entirety.

TECHNICAL FIELD

The application belongs to the field of biotechnology, and in particular relates to a negative regulator AtRTP5 and use thereof in the plant resistance to *Phytophthora*.

BACKGROUND

Oomycetes are a class of eukaryotic pathogenic microorganisms, including a variety of pathogenic bacteria and involving a wide range of hosts, which can cause various diseases to crops and ornamental plants, and thus results in huge economic losses. In the 1850s, the potato late blight caused by *Phytophthora infestans* in Oomycetes led to the widespread death of potato crops in Europe, and thus made hundreds of thousands of people die from starvation. Tobacco black shank, one of the major tobacco diseases worldwide, occurs in various major tobacco-producing areas of China to varying degrees, which causes devastating damage to tobacco production and seriously compromises the economic income and life quality of local tobacco farmers. The pathogen causing tobacco black shank is *Phytophthora parasitica* in Oomycetes. In the production, the potato late blight and tobacco black shank are most controlled by treating with agrochemicals or developing disease-resistant varieties. However, due to the emergence of agrochemical-resistance of pathogens and the coevolution of plants with pathogenic microorganisms, the effective development of disease-resistant resources and the cultivation of resistant varieties are still the top priority for the research effort at present.

The identification and application of disease-resistant genes is the preferred way to control crop diseases. In the process of plant-pathogen compatible interaction, some plant genes are often up-regulated in expression after being induced by pathogens, which often serve as "helpers" for pathogens to successfully infect plants, and are called negative regulators of plant immunity. The deletion or functional mutation of a negative regulatory factor for immunity can make plants acquire resistance, which exhibits broad-spectrum disease-resistance by inhibiting the infection and colonization of pathogens.

Although a few negative regulators of plant immunity have been identified at present, the specific action mechanism is not clear, and the use of a negative regulatory factor for immunity in the breeding of disease-resistant varieties is even rarer.

SUMMARY

One embodiment is to solve at least the above-mentioned problems and provide at least the advantages to be described later.

Another embodiment is to provide use of a negative regulator of AtRTP5 gene for plant immunity in the resistance to *Phytophthora*.

This application is related to providing the use of a negative regulator AtRTP5 for increasing the plant resistance to *Phytophthora*. The AtRTP5 gene negatively regulates the plant resistance to *Phytophthora* by interfering with plant hormone immune signaling pathways.

The AtRTP5 gene has a nucleotide sequence shown as SEQ ID NO: 1 or a homologous sequence having more than 50% homology with the sequence shown as SEQ ID NO: 1.

This application is also related to providing the use of a protein encoded by the negative regulator AtRTP5 for increasing the plant resistance to *Phytophthora*. The plant resistance to *Phytophthora* is enhanced by reducing the expression of the protein encoded by the AtRTP5 gene with genetic engineering.

The protein has an amino acid sequence shown as SEQ ID NO: 2 or a homologous sequence having more than 50% homology with the sequence shown as SEQ ID NO: 2.

Preferably, the homologous sequence is derived from potato or tobacco.

Preferably, the plant is *Arabidopsis thaliana*, potato or tobacco.

The subject matter disclosed herein has at least the following beneficial effects: In some embodiments, the negative regulator AtRTP5 is cloned as a negative regulatory factor affecting the plant immunity for the first time. A transgenic *Arabidopsis thaliana* material overexpressing the AtRTP5 gene is constructed through genetic engineering, and then tested by the in-vitro leaf inoculation experiment, and the results prove that the AtRTP5 gene-overexpressing *Arabidopsis thaliana* is more susceptible to *Phytophthora parasitica*. Moreover, an AtRTP5 T-DNA insertion mutant purchased from the *Arabidopsis thaliana* Resource Center is tested through the inoculation experiment, and it is found that the mutant has significantly-increased resistance to *Phytophthora parasitica*. The above results fully confirm that the overexpression of the AtRTP5 gene (as a negative regulatory gene) can make the plant more susceptible to *Phytophthora*, and if the expression of this gene is reduced, the plant will have enhanced resistance to *Phytophthora*. Therefore, the negative regulator AtRTP5 is used as a negative regulatory factor affecting the plant immunity for the first time, which has important values and guiding significance for the cultivation of new plant varieties resistant to *Phytophthora*.

Other advantages, objects and features of the disclosed subject matter will be partially embodied through the following description, and some will be understood by those skilled in the art.

BRIEF DESCRIPTION OF DRAWINGS

FIG. 3 illustrates the results of the sequence alignment between AtRTP5 in one embodiment and homologous protein, where the amino acid sequences are respectively for NbRTP5-1(SEQ ID NO: 7), NbRTP5-2(SEQ ID NO: 8), NbRTP5-3(SEQ ID NO: 9), NbRTP5-4(SEQ ID NO: 10), AtRTP5(SEQ ID NO: 2).

FIG. 4 illustrates the results of the sequence alignment between AtRTP5 in one embodiment and homologous protein, where the amino acid sequences from top to bottom are respectively for XP_0151679(GenBank Accession Number XP_015167964.1, SEQ ID NO:22), XP_0151679(GenBank Accession Number XP_015167963.1, SEQ ID NO:21), XP_0063408(GenBank Accession Number XP_006340895.1, SEQ ID NO:20), AtRTP5(SEQ ID NO: 2).

DETAILED DESCRIPTION

Different embodiments will be further described in detail below.

It should be understood that the terms, such as "have", "include" and "comprise" as used herein, do not exclude the presence or addition of one or more other elements or a combination thereof.

Example 1 Cloning of the *Arabidopsis thaliana* Negative Regulator AtRTP5

1. Plant material: wild-type *Arabidopsis thaliana* Col-0 (available from public channels), where RNA was extracted from the leaves of the *Arabidopsis thaliana*.

2. RNA Extraction

RNA was extracted with an RNA extraction kit (OMGA). The integrity of the RNA was identified by agarose gel electrophoresis. Then the purity and concentration of the RNA were determined on a spectrophotometer.

3. Gene Cloning

A reverse transcription kit (TaKaRa) was used to obtain the cDNA of Col-0, and the upstream and downstream primers (AtRTP5-F/R) were designed according to the full-length coding sequence (CDS) of AtRTP5 (At5G43930) provided in The *Arabidopsis* Information Resource (TAIR):

```
AtRTP5-F:
                               (SEQ ID NO: 11)
5'-CCGGAATTCATGACTCAATCTATCTGTTCGTC-3'

AtRTP5-R:
                               (SEQ ID NO: 12 )
5'-GCGCGGATCCTTAGGTGTTTGGTCCTGTG-3',
```

Figure 5:
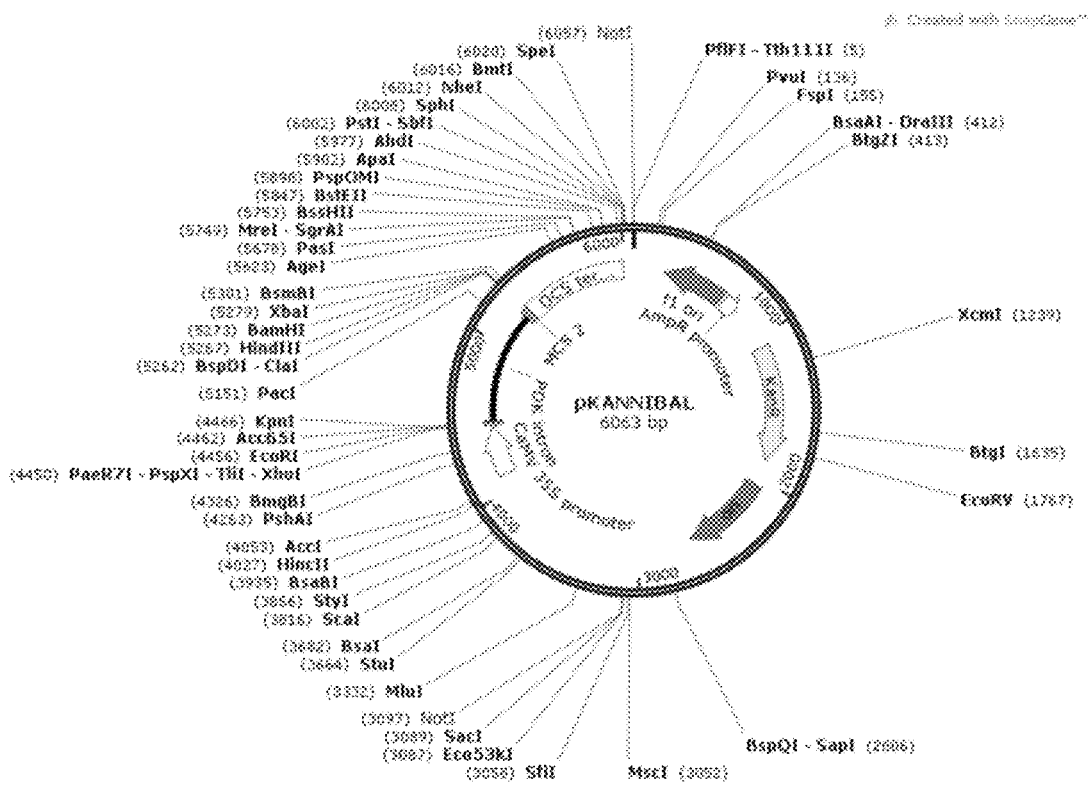
FIG. 5 illustrates the pKannibal vector map in one embodiment.

The cDNA was used as a template for amplification. The PCR amplification product was constructed into a vector pKannibal through digestion, ligation and colony PCR identification (see FIG. 5 for the pKannibal plasmid vector map), and then sent for sequencing. The sequencing results were compared with the published sequences, and the correct plasmid was used for the subsequent experiments.

Example 2 the Sequence Information and Homology Analysis for the *Arabidopsis thaliana* AtRTP5 Gene The *Arabidopsis thaliana* AtRTP5 gene in one embodiment has a full-length CDS of 2,181 bp, and the detailed sequence is shown as TAIR Gene Locus: At5G43930.1 (see SEQ ID NO: 1). The amino acid sequence has 726 amino acids in total, and the detailed sequence is shown as TAIR Accession AASequence NO.: 1009128620 (see SEQ ID NO: 2).

The amino acid sequence of the protein encoded by the *Arabidopsis thaliana* AtRTP5 gene was subjected to homology search with the BLAST program, and it was found that the AtRTP5 gene had high homology with four genes of NbRTP5-1/NbRTP5-2/NbRTP5-3/NbRTP5-4 (with nucleotide sequences shown as SEQ ID NO: 3 to SEQ ID NO: 6 in detail) in *Nicotiana benthamiana*. The amino acid sequences encoded by the four genes had more than 50% homology with the amino acid sequence encoded by the AtRTP5 gene, and had biological functions similar to the amino acid sequence encoded by the AtRTP5 gene. The amino acid sequences encoded by the homologous genes were shown in Sequence IDs (obtained according to Sol Genomics Network blast tool) of Niben101Scf00274g03001.1, Niben101Scf05619g00010.1, Niben101Scf11483g00012.1 and Niben101Scf02842g-01008.1 (see SEQ ID NO: 7, SEQ ID NO: 8, SEQ ID NO: 9 and SEQ ID NO: 10 for details).

Moreover, three genes (GenBank Accession Number: NW_006239128.1, NW_006239128.1 and NW_006238946.1) were also found in the genome of potato to have high homology with the AtRTP5 gene. The amino acid sequences encoded by these genes were shown in GenBank Accession Number: XP_015167963.1, XP_015167964.1 and XP_006340895.1, and had more than 50% homology with the amino acid sequence encoded by the AtRTP5 gene. It can be concluded from the above that the seven homologous genes have the same or similar functions as AtRTP5.

The alignment results of the amino acid sequence encoded by the *Arabidopsis thaliana* AtRTP5 gene in one embodiment and the amino acid sequences encoded by the four homologous genes in *Nicotiana benthamiana* are shown in FIG. 3.

The alignment results of the amino acid sequence encoded by the *Arabidopsis thaliana* AtRTP5 gene in one embodiment and the amino acid sequences encoded by the three homologous genes in the sequenced genome of potato are shown in FIG. 4.

Example 3 Acquisition of AtRTP5-Overexpressing Transgenic *Arabidopsis thaliana*

Construction of a Vector pART27::AtRTP5-Flag for Gene Expression

The upstream and downstream primers (AtRTP5-F/R) were designed according to the full-length CDS of AtRTP5

(At5G43930) provided in The *Arabidopsis* Information Resource (TAIR):

```
AtRTP5-F:
                                       (SEQ ID NO: 11)
5'-CCGGAATTCATGACTCAATCTATCTGTTCGTC-3'

AtRTP5-R:
                                       (SEQ ID NO: 12)
5'-GCGCGGATCCTTAGGTGTTTGGTCCTGTG-3',
```

The cDNA of *Arabidopsis thaliana* Col-0 was used as a template for amplification. The PCR product was digested with an endonuclease and then ligated to the vector pKannibal (available from public channels), and then electroporated into competent *E. coli*, and positive clones were screened on a kanamycin-resistant plate. The vector primer pKAN-F/R:

```
pKAN-F:
                                       (SEQ ID NO: 13)
5'-CAATCCCACTATCCTTCGCA-3' pKAN-R:
                                       (SEQ ID NO: 14)
5'-CGGTAAGGATCTGAGCTACA-3'
``` was used to carry out the colony PCR to identify the correct clones, and then the plasmid was extracted and sent to a sequencing company for sequencing.

Figure 6:
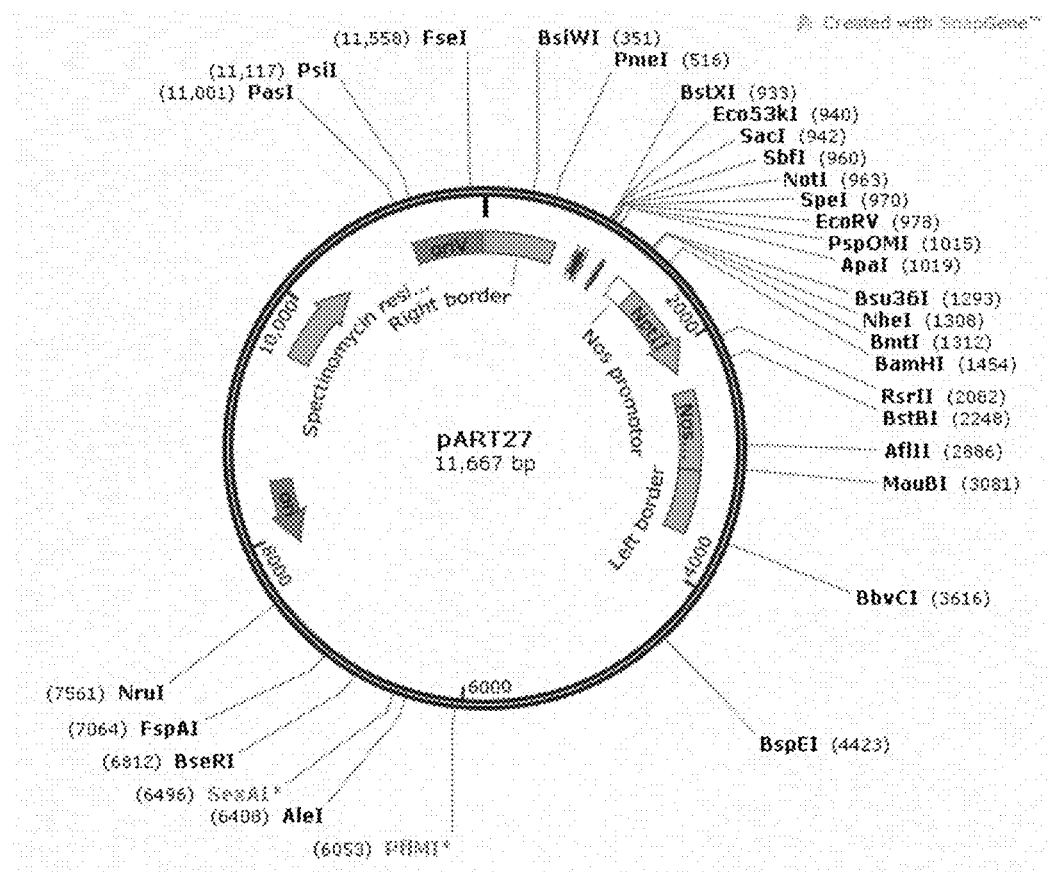
FIG. 6 illustrates the pART27 vector map in one embodiment.

The sequencing results were compared with the published sequences. The correct plasmid was digested with an endonuclease NotI, then ligated to the vector pART27 (available from public channels, with a vector map shown in FIG. 6), and electroporated into competent *E. coli*. The correct clones were screened on a spectinomycin-resistant plate, and the plasmid was extracted for enzyme digestion identification. The plasmid identified as correct was electroporated into competent *Agrobacterium tumefaciens*, and then positive clones were screened on a resistant plate.

The *Agrobacterium tumefaciens*-mediated floral dipping was adopted to conduct *Arabidopsis thaliana* transformation, and the specific steps were as follows:
1. The vector pART27::AtRTP5-Flag for gene expression was electroporated into competent *Agrobacterium tumefaciens*, and the successfully-transformed clones were inoculated into a liquid LB medium and cultivated for 24 h to 36 h.
2. The fresh bacterial solution was inoculated into 200 mL of LB liquid medium at a ratio of 1:100 for amplification culture, and then cultivated overnight for about 16 h.
3. The bacterial cells were collected by centrifugation at low speed, and then resuspended with the same volume of 5% sucrose solution including 0.02% surfactant.
4. The pods of the wild-type *Arabidopsis thaliana* were cut off, and the unopened flower buds were soaked in the resuspended bacterial solution for 15 s to 30 s, and subjected to moisturizing treatment overnight in the dark.
5. The first-generation seeds were harvested after about 1 month of cultivation in the plant cultivation room, and then dried, and the successfully-transformed plants were screened on a resistant plate. The successfully-transformed plants could grow normally on the resistant plate, with a growth state and rate consistent with normal plants. The expression of the target gene was detected in the successfully-transformed plants, and more than 50% of the plants could overexpress the target gene (at an expression level more than 6 times higher than that of the wild-type plant).

Example 4

Acquisition of tobacco homologous gene NbRTP5-silenced plants and inoculation experiment The virus-mediated gene-silencing technology was adopted to reduce the expression of the target gene, and the specific implementation was as follows:
1. Construction of a Vector TRV2-Nb4RTP5 for Silencing Expression.

The amino acid sequence of AtRTP5 was used for sequence alignment on the Sol Genomics Network, and four homologous genes of NbRTP5-1/NbRTP5-2/NbRTP5-3/NbRTP5-4 (see SEQ ID NO: 3 to SEQ ID NO: 6 for details) were found in *Nicotiana benthamiana*. The VIGS tool provided by the website was used to find two specific sequences that could simultaneously silence these four genes, then PCR primers were designed according to the sequences, and the cDNA of *Nicotiana benthamiana* was used as a template for sequence amplification. The two sequences were fused into a sequence fragment Nb4RTP5 by fusion PCR, which was then digested, purified, and ligated to the vector pTRV2 (available from public channels). The sequence accuracy was verified by sequencing.

The target sequence selected for simultaneously silencing the four homologous genes of *Nicotiana benthamiana* is as follows:

```
                                       (SEQ ID NO: 15)
TGCATCTGTCCGACTTCTCACTTACTCAACTCCTTCTGGCCAATATGAAC

TTTTGTTGTCCCCTGTTGAGCCAACTTTATCTCCTGCACAAGCTCAGACT

GGTTCTTCTGTTAGGAATATTGAGAATGCATCCGAACCTGTAGTTGATCC

TATGGATACTGATGTGCCGGCTGAGGAAAGAAACAATCAATTTTTCCCTT

GAAAATTTTGGGGTGAGAACACTAAATGTACTCTTGACTCCTGTGGATTA

AAAAGTGAAGTGGCAAGTGATGCTAGACGGGGACTAATATCATGGGTAGA

GGCGGAGTCACTGCAACATTTATCGGCCAAGTATTGTTCACTGTTGCCTC

CTCCAAGGTCTACCATTGCAGCAGCATTCAGTCCTGATGGGAGGACACTT
```

The primers required to amplify the above target sequence are as follows:

```
tNbRTP5-1F:
                                       (SEQ ID NO: 16)
GTTACCGAATTCTCTAGA TGCATCTGTCCGACTTCTCAC tNbRTP5-1R:
                                       (SEQ ID NO: 17)
CAAAATTTTCAAGGGAAAAATTGATTGTTTCTTTCC tNbRTP5-2F:
                                       (SEQ ID NO: 18)
TTTTTCCCTTGAAAATTTTGGGGTGAGAACACT tNbRTP5-2R:
                                       (SEQ ID NO: 19)
GAGCTCGGTACCGGATCC AAGTGTCCTCCCATCAGGACT.
```

2. The vector TRV2-Nb4RTP5 for silencing was electroporated into competent *Agrobacterium tumefaciens*, and the successfully-transformed clones were inoculated into a liquid LB medium and cultivated for 24 h to 36 h.

3. The bacterial cells were collected at low speed, and then resuspended with an MES solution including acetosyringone, and a part of the bacterial solution was taken and diluted for OD600 determination by a spectrophotometer.

4. The bacterial solution was adjusted to an appropriate concentration and then mixed with the TRV1 bacterial solution for injection.

5. *Nicotiana benthamiana* seedlings at the 4 to 6 leaf stages were selected, and a 1 mL needle-free syringe was used to inject the mixed solution at the back of the largest leaf. 2 to 3 weeks later, the leaves that were two leaf positions higher than the injected leaf were selected for the inoculation experiment.

Figure 2:
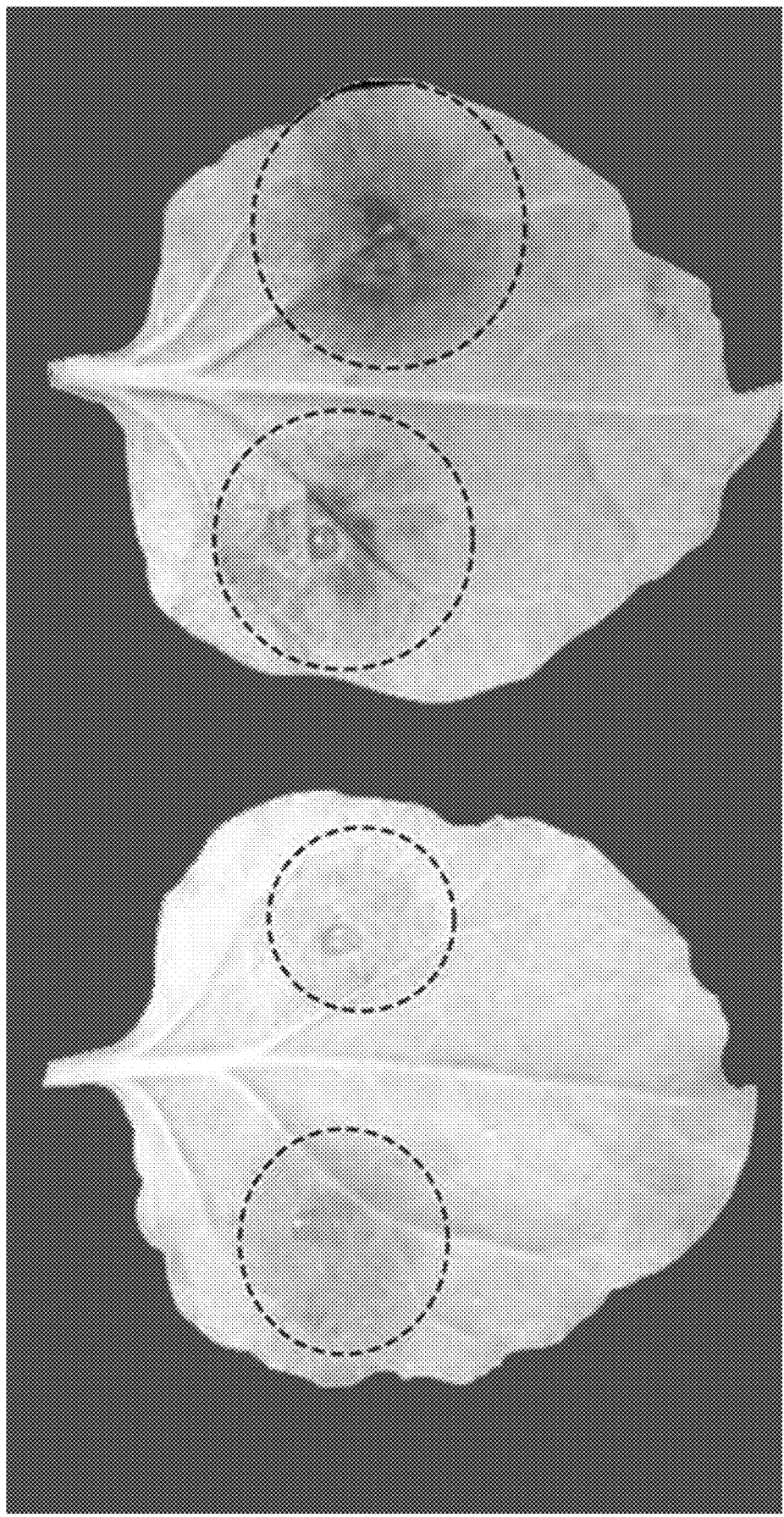
FIG. 2 illustrates that the tobacco homologous gene NbRTP5-silenced plant in one embodiment is resistant to the infection of *P. parasitica*.

6. The *Phytophthora parasitica* inoculation experiment was specifically as follows: the salt-cultivated *Phytophthora parasitica* was stimulated with cold water, then placed at 4° C. for 0.5 h, and then transferred to a 23° C. incubator for 1 h of release. Zoospores, after released, were counted under a microscope and then diluted to a concentration of 50 zoospores/μL to 80 zoospores/μL. 10 μL of the zoospore suspension was inoculated at the back of in-vitro leaves. The leaves were sprayed with water and then dried with paper to prevent the zoospore suspension from scattering before the inoculation, and the large leaf veins were avoided during the inoculation. The infection of the pathogenic bacteria was observed 2 to 3 days after inoculation, and the diameters of the diseased spots were recorded. As shown in FIG. 2, the results show that the diseased spots on the leaves of Nb4RTP5-silenced plants are smaller and more resistant to the infection of *Phytophthora parasitica*.

Example 5 Functional Study of the AtRTP5 Gene

AtRTP5 T-DNA insertion mutant rtp5-3 purchased from the *Arabidopsis thaliana* Resource Center and AtRTP5-overexpressing transgenic *Arabidopsis thaliana* were used for inoculation experiment. Rosette leaves of *Arabidopsis thaliana* at 25 to 28 days old were selected and lightly scratched at the back, and then 8 μL to 10 μL (about 3,000) of *Phytophthora parasitica* zoospore suspension was inoculated. The inoculated leaves were subjected to moisturizing treatment in a 23° C. incubator for 2 to 3 days in the dark, then the incidence was observed and recorded.

The inoculation experiment of AtRTF5-overexpressing tobacco leaves: the *Agrobacterium tumefaciens* suspension including the plasmid pART27::AtRTP5-Flag was injected at one side of the leaf of *Nicotiana benthamiana* at 6 to 8 weeks old, and the *Agrobacterium tumefaciens* suspension including the control plasmid (pART27::Flag-GFP, constructed by the same method as pART27::AtRTP5-Flag) was injected at the other side. The injection areas on both sides were ensured to be similar, and both not cross the middle main vein. The plant was subjected to moisturizing treatment overnight in the dark, and then the injected leaf was cut off after the plant was normally cultivated in the plant cultivation room for 2 days. 8 μL to 10 μL (about 500) of *Phytophthora parasitica* zoospore suspension was inoculated near the injection hole, then the leaf was subjected to moisturizing treatment in a 23° C. incubator for 2 to 3 days in the dark, and the incidence was observed and recorded. Or, 10 μL to 15 μL (about 1,000) of *Phytophthora infestans* zoospore suspension was inoculated near the injection hole, then the leaf was subjected to moisturizing treatment in a 18° C. incubator for 5 days in the dark, and the incidence was observed and recorded.

Figure 1A:
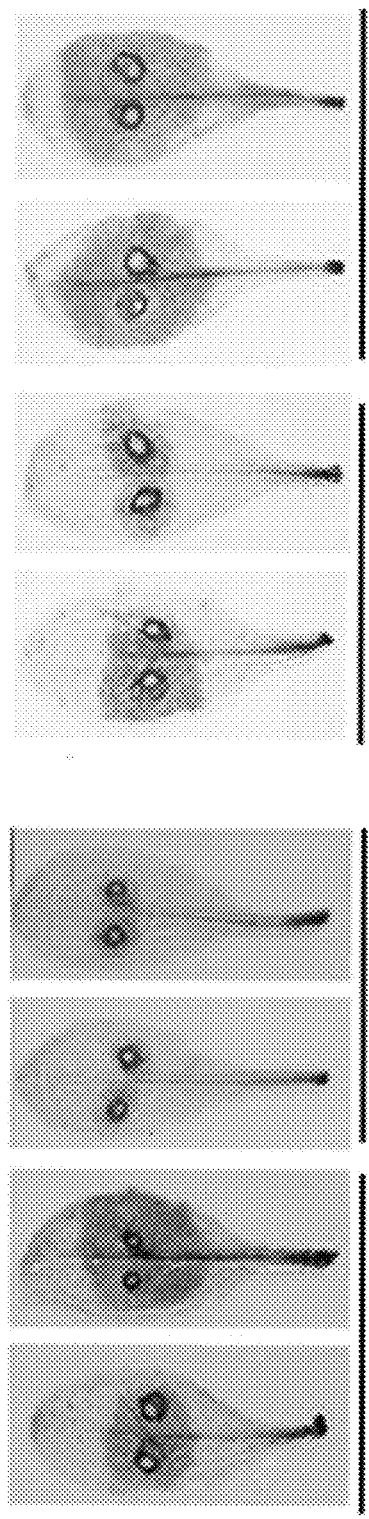
FIG. 1A illustrates that, in one embodiment, the AtRTP5 T-DNA insertion mutant rtp5-3 is resistant to the infection of *P. parasitica*.
Figure 1B:
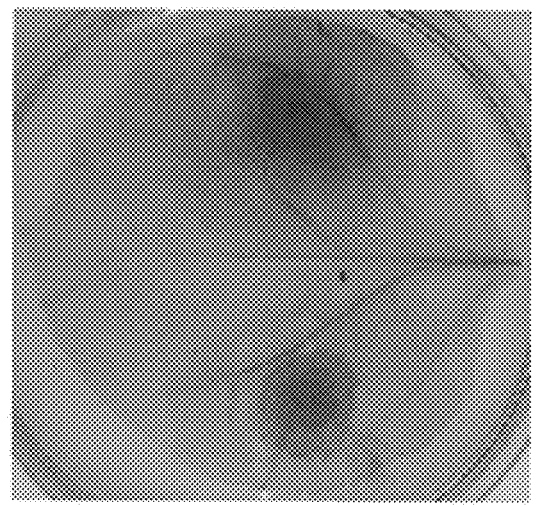
FIG. 1B illustrates that in one embodiment, the AtRTP5-overexpressing plant RTP50E2 is more susceptible to the infection of *P. parasitica*.
Figure 1C:
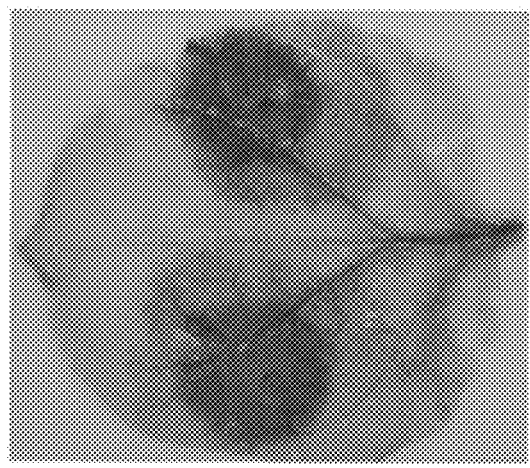
FIG. 1C illustrates that in one embodiment, the transient overexpression of AtRTP5 in tobacco promotes the infection of *Phytophthora parasitica* and *Phytophthora infestans*.

As shown in FIG. 1, whether inoculated with *Phytophthora parasitica* or *Phytophthora infestans*, the leaves of the AtRTP5-overexpressing plant have larger diseased spots and are more susceptible to disease.

The above implementations are merely intended to illustrate different embodiments. Although the different embodiments are described in detail with reference to the examples, those of ordinary skill in the art should understand that various combinations, modifications or equivalent substitutions may be made to these embodiments.

What is claimed is:

1. A method for increasing plant resistance to *Phytophthora*, comprising:
   constructing a vector comprising a fragment comprising SEQ ID NO: 15; and introducing the vector to the plant.
2. The method of claim 1, wherein the plant is *Arabidopsis thaliana*, potato or tobacco.

* * *

SEQUENCE LISTING

<160> NUMBER OF SEQ ID NOS: 22

<210> SEQ ID NO 1
<211> LENGTH: 2181
<212> TYPE: DNA
<213> ORGANISM: Arabidopsis thaliana

<400> SEQUENCE: 1

```
atgactcaat ctatctgttc gtcgtcacaa gatcaatctt cttctcctcg ctctttgatc      60
acaccacgca aatcggcgac gaagtttcac cgccgcaggg ggaggagtgt atttaacatg     120
ctggttcaga gggaaatgtc accaaaggct aagtttgtgc caaggaaacg atggggtaag     180
agtagatggt atactgattc ttcatgcgga accaacaacg agtctatgaa agagacggga     240
caaagtctta cctcatgggt tgaggcagag tcattgcagc atttatctgc aaaatattgt     300
cctcttggag ctcctccaag gtcaactatt gctgcggctt ttagtactga tggaagaact     360
cttgcttcta cacatggtga tcatactgtg aagattattg attgtgaaac tggaaactgc     420
ttaaaagttt tgactggcca taggaggact ccttgggtag tcagattcca cccgcatcat     480
tcagaaatag ttgcgagtgg aagtttagat ctcgaggtcc gcttatggaa taccacaact     540
tctgaatgca ttagatctca tctattctat cggcctattg cttctatcgc tttccatgct     600
gagggtgaac tacttgctgt tgcttctggt cataagctgc acatgtggca ctacaatagg     660
```

```
agaggagagg gatcatcacc aactgttgta ttgaagacga ggcgatcttt gagagctgta    720
cactttcacc ctcatggggc tccattactt ttgaccgcag aggtgaatga gattgattca    780
ttagattctt caatgtctag agcaacatct atgggctact tgaggtatcc gccccctgct    840
attttgttca caagcacgga aagcaatcaa actagtttgg cagcagaaaa tgagaacaga    900
acatcgtctc ctcctcttcc cttggctaca tccagtggtc cttctggtcc aaatagtgtt    960
ccaggaaatt ctcccagcaa catatttctt acccgagctg gagatagaac ttctcctgca   1020
gttgatggca tggatgtaga tgaagctcaa cctgttggaa gaaatggaat ccctagccaa   1080
gtttcaaata gatcagattt ccctgagctt ggacagattc ggcaattatt tcactttagg   1140
gatcgagttt cctgggagtt accttttcta caaggatggt tgatggctca aggtcatggt   1200
gttgctaatc cagtggttac tcctactggc agtagtaatc atggcatctc agctccatcc   1260
tcaacagcca gtctggaggc tgcagtagcg ttattagaaa tcccgagtgg tgttaactta   1320
catgcggtgt ctagaagagg cggggctcag gaacaaactt cacaaccccca attctcgaga   1380 actggattac cggaaggtgt atcttctcgt aacactcaac atggaagtga tgctcaacct   1440
gtagtaaata gggtccagtc tgagcttgct acctcaattg ctgcttcggc tgcagcagct   1500
gctgctgcag aattaccttg tactgtcaaa ctcagaatgt ggtcgcatga catcaaagac   1560
ccatatgcac aactgaaatc cgacagatgt ctatttacaa taccgcatgc cgtcctttgc   1620
agtgaaatgg gagctcatta ttcgccatgt gggagatatt tagcggcctg tgttgcgtgt   1680
gtttttcctc atggtgagat agatcctgga ctgcagacac aagctcaaca agattcaggg   1740
cttgcaactt ccccaactcg acaccctgtc acagcacacc aagtcattta cgagcttcgt   1800
gtgtattctc tccagaagga aagttttggt tcagtacttg tgtcacgggc aattagagct   1860
gcacattgct tgacctctat ccagttctca cccacttcgg agcatatact acttgcatat   1920
gggcggcgtc atggttctct tttgaggagc atcgttagtg atggtgaaac aacatcacat   1980
tttttcacag tattggagat atacagagtt tcagatatgg agcttgtgag agtactgcca   2040
agttcagagg atgaagtgaa cgttgcgtgt tttcatcctt ctcctggagg aggtcttgtt   2100
tatgggacaa aggagggaa actgaggatc ttccagtaca atacagctgc tacctcaaac   2160
ttcacaggac caaacaccta a                                             2181
```

<210> SEQ ID NO 2
<211> LENGTH: 726
<212> TYPE: PRT
<213> ORGANISM: Arabidopsis thaliana

<400> SEQUENCE: 2

```
Met Thr Gln Ser Ile Cys Ser Ser Gln Asp Gln Ser Ser Ser Pro
1               5                   10                  15

Arg Ser Leu Ile Thr Pro Arg Lys Ser Ala Thr Lys Phe His Arg Arg
            20                  25                  30

Arg Gly Arg Ser Val Phe Asn Met Leu Val Gln Arg Glu Met Ser Pro
        35                  40                  45

Lys Ala Lys Phe Val Pro Arg Lys Arg Trp Gly Lys Ser Arg Trp Tyr
    50                  55                  60

Thr Asp Ser Ser Cys Gly Thr Asn Asn Glu Ser Met Lys Glu Thr Gly
65                  70                  75                  80

Gln Ser Leu Thr Ser Trp Val Glu Ala Glu Ser Leu Gln His Leu Ser
                85                  90                  95
```

-continued

```
Ala Lys Tyr Cys Pro Leu Gly Ala Pro Pro Arg Ser Thr Ile Ala Ala
            100                 105                 110
Ala Phe Ser Thr Asp Gly Arg Thr Leu Ala Ser Thr His Gly Asp His
        115                 120                 125
Thr Val Lys Ile Ile Asp Cys Glu Thr Gly Asn Cys Leu Lys Val Leu
    130                 135                 140
Thr Gly His Arg Arg Thr Pro Trp Val Val Arg Phe His Pro His His
145                 150                 155                 160
Ser Glu Ile Val Ala Ser Gly Ser Leu Asp Leu Glu Val Arg Leu Trp
                165                 170                 175
Asn Thr Thr Thr Ser Glu Cys Ile Arg Ser His Leu Phe Tyr Arg Pro
            180                 185                 190
Ile Ala Ser Ile Ala Phe His Ala Glu Gly Glu Leu Leu Ala Val Ala
        195                 200                 205
Ser Gly His Lys Leu His Met Trp His Tyr Asn Arg Arg Gly Glu Gly
    210                 215                 220
Ser Ser Pro Thr Val Val Leu Lys Thr Arg Arg Ser Leu Arg Ala Val
225                 230                 235                 240
His Phe His Pro His Gly Ala Pro Leu Leu Leu Thr Ala Glu Val Asn
                245                 250                 255
Glu Ile Asp Ser Leu Asp Ser Ser Met Ser Arg Ala Thr Ser Met Gly
            260                 265                 270
Tyr Leu Arg Tyr Pro Pro Pro Ala Ile Leu Phe Thr Ser Thr Glu Ser
        275                 280                 285
Asn Gln Thr Ser Leu Ala Ala Glu Asn Glu Asn Arg Thr Ser Ser Pro
    290                 295                 300
Pro Leu Pro Leu Ala Thr Ser Ser Gly Pro Ser Gly Pro Asn Ser Val
305                 310                 315                 320
Pro Gly Asn Ser Pro Ser Asn Ile Phe Leu Thr Arg Ala Gly Asp Arg
                325                 330                 335
Thr Ser Pro Ala Val Asp Gly Met Asp Val Asp Glu Ala Gln Pro Val
            340                 345                 350
Gly Arg Asn Gly Ile Pro Ser Gln Val Ser Asn Arg Ser Asp Phe Pro
        355                 360                 365
Glu Leu Gly Gln Ile Arg Gln Leu Phe His Phe Arg Asp Arg Val Ser
    370                 375                 380
Trp Glu Leu Pro Phe Leu Gln Gly Trp Leu Met Ala Gln Gly His Gly
385                 390                 395                 400
Val Ala Asn Pro Val Val Thr Pro Thr Gly Ser Ser Asn His Gly Ile
                405                 410                 415
Ser Ala Pro Ser Ser Thr Ala Ser Leu Glu Ala Ala Val Ala Leu Leu
            420                 425                 430
Glu Ile Pro Ser Gly Val Asn Leu His Ala Val Ser Arg Arg Gly Gly
        435                 440                 445
Ala Gln Glu Gln Thr Ser Gln Pro Gln Phe Ser Arg Thr Gly Leu Pro
    450                 455                 460
Glu Gly Val Ser Ser Arg Asn Thr Gln His Gly Ser Asp Ala Gln Pro
465                 470                 475                 480
Val Val Asn Arg Val Gln Ser Glu Leu Ala Thr Ser Ile Ala Ala Ser
                485                 490                 495
Ala Ala Ala Ala Ala Ala Ala Glu Leu Pro Cys Thr Val Lys Leu Arg
            500                 505                 510
Met Trp Ser His Asp Ile Lys Asp Pro Tyr Ala Gln Leu Lys Ser Asp
```

|  | 515 |  | 520 |  | 525 |  |
|---|---|---|---|---|---|---|

Arg Cys Leu Phe Thr Ile Pro His Ala Val Leu Cys Ser Glu Met Gly
530 535 540

Ala His Tyr Ser Pro Cys Gly Arg Tyr Leu Ala Ala Cys Val Ala Cys
545 550 555 560

Val Phe Pro His Gly Glu Ile Asp Pro Gly Leu Gln Thr Gln Ala Gln
565 570 575

Gln Asp Ser Gly Leu Ala Thr Ser Pro Thr Arg His Pro Val Thr Ala
580 585 590

His Gln Val Ile Tyr Glu Leu Arg Val Tyr Ser Leu Gln Lys Glu Ser
595 600 605

Phe Gly Ser Val Leu Val Ser Arg Ala Ile Arg Ala Ala His Cys Leu
610 615 620

Thr Ser Ile Gln Phe Ser Pro Thr Ser Glu His Ile Leu Leu Ala Tyr
625 630 635 640

Gly Arg Arg His Gly Ser Leu Leu Arg Ser Ile Val Ser Asp Gly Glu
645 650 655

Thr Thr Ser His Phe Phe Thr Val Leu Glu Ile Tyr Arg Val Ser Asp
660 665 670

Met Glu Leu Val Arg Val Leu Pro Ser Ser Glu Asp Glu Val Asn Val
675 680 685

Ala Cys Phe His Pro Ser Pro Gly Gly Leu Val Tyr Gly Thr Lys
690 695 700

Glu Gly Lys Leu Arg Ile Phe Gln Tyr Asn Thr Ala Ala Thr Ser Asn
705 710 715 720

Phe Thr Gly Pro Asn Thr
725

```
<210> SEQ ID NO 3
<211> LENGTH: 2310
<212> TYPE: DNA
<213> ORGANISM: Artificial Sequence
<220> FEATURE:
<223> OTHER INFORMATION: NbRTP5-1

<400> SEQUENCE: 3
atgagggcgt cactttggcc ggagaattca agcagtgatt catccacgtc aatttcgcgg      60
cggcggaatt cgccacctca ttccatttcc caaaaccccta attgtaaaca cagctgcggt     120 aacgttttc agttgctaac gaggagggag gtatctcctc gaactaaacg cagttctacg      180 aagtttggg gtgagaactc taaatgttca gtttattcct gtggattaaa aagccaagta     240
gcaagagacc cgagacaggg tcttatatca tgggtagagg cagagtcatt gagacatttt     300
tcagctaagt attgtccact gttgcctccg cccaggtcca ctattgctgc ggcattcagt     360
cctgatggga agacactcgc ttctactcat ggagatcaca cagtaaagat aattgattgc     420
caaagtggaa agtgcttaaa ggtgttaagt ggacatcgca ggactccttg ggtggttcgt     480
ttccatccgt tatactctga tatacttgca agtggaagtt tggaccatga agttcgtcta     540
tgggatgcaa agactgccga gtgtatagga tcacatcgtc ctattgcatc cattgccttc     600
catgcccaag ggaagttttt ggctgttgct tcaggccaca agctgtatat gtggcactac     660
aacagaagag gggaagcatc ttccaccagct atcgtactaa agacaagacg ttcacttcgt     720
gctgtacatt ttcacccaca tggtgcccca tttcttttaa cagctgaggt caatgatttg     780
gactcatcag attcttcaat gacgcttgca acttctccgg gtaacttgcg gtaccctcct     840
```

```
cctactgtgt atttgacaga tgctcactcc acttaccgat ctgcttcagc aaatgaattg    900
ccgatcatgt ctctaccatt catgatctgg ccttcaatcg ctagaggtga tcctggaatg    960
cctttgcagc agagcgatgc agacatggct tctgacagca cacagcacag agcggacact   1020
tatgcatctg tccgacttct cacttactca actccttctg gccaatatga acttttgttg   1080
tccctgttg agccaacttt atctcctgca caagctcaga ctggttcttc tgttaggaat   1140
attgagaatg catccgaacc tgtagttgat cctatggata ctgatgtgcc ggctgaggaa   1200
agaaacaatc aattttctcc tttcagtgac cctgcatact gggaattacc tttcttgcaa   1260
ggatggttga ttggccaaag ccaagctggc cggcgagcga ttcattcaga gcacagtggt   1320
gccacaagta gtgtatcggc ttatggtgaa gtagaacatc ctcctgcagt tccgtcagtc   1380
atttcaaaca gtaatcattc aaggtctgga agatctggtt ctcgtcaccg ttcttcacgc   1440
tctagagcga tacctgttgt tggatctggt gatagcgctg ctcccattaa cgttgtacat   1500
gatgaaaatg attctcaagc ttttatgagt cagttccagt cagagatagc cacttcactg   1560
gctgcagcag cggctcccga attgccttgc actgtgaaac tcagaatatg gccttatgat   1620
gttaaggctc catgtgcacc gcttgatgct gaaaattgtc gcttaatgat accacatgct   1680
gtgctttgta gtgaaatggg agcccacttt tcaccatgtg ggagattttt agcagcttgt   1740
gttgcatgta ttctgcctaa catggaagct gaacctggtt tcacggaca acttcaccat   1800
gatgccatgg gtgctgcaac ttcacctacc agacatccta ttgcagccca tcgggttatg   1860
tatgagctac gaatatattc cttggaggag gcaacgtttg gtttagtgct tgtatctcgg   1920
gcaattagag ctgcacattg tttgacttca attcagtttt ctccaacttc tgaacatctt   1980
ttacttgcct atgggcgtcg gcacggttca cttctgaaaa gtatagtggt tgatggagat   2040
acaactgtac ccgtttacac gattcttgag gtctacagag tttcagatat ggaacttgtg   2100
agagttcttc ccagtgcaga ggatgaggtt aacgttgctt gtttccatcc tttggttggt   2160
ggcggcctag tctatggaac caaggaagga aaattgagga tcctccaatt tgataaatca   2220
aatgggtgtc atgaaaatat acgtatcagg acaatgactg gtggctgcaa agttgaatgt   2280
gttgctgatg gtgactgtat agttagttga                                    2310

<210> SEQ ID NO 4
<211> LENGTH: 2100
<212> TYPE: DNA
<213> ORGANISM: Artificial Sequence
<220> FEATURE:
<223> OTHER INFORMATION: NbRTP5-2

<400> SEQUENCE: 4
atgagatcgt ctgtcttgcc ggagaattca ggcagtgcgc cgtcaacttc gcggaattca     60
cctccttctg cgacggcgcc tcgaaactcc aattgtaaac acagtaatgt ctttcaactg    120
ttaacaagaa gggaggtatc ttctcgaact aaacgcgctt ccagaaaatt ttggggtgag    180
aacactaaat gtactcttga ctcctgtgga ttaaaaagtg aagtggcaag tgatgctaga    240
cgggactaa tatcatgggt agaggcggag tcactgcaac atttatcggc caagtattgt     300
tcactgttgc ctcctccaag gtctaccatt gcagcagcat tcagtcctga tgggaggaca    360
cttgcttcta cgcatggaga tcacacagtg aaaataattg actgtcaaac tgggaagtgc    420
ttaaaggttt tgagtggaca ccgcaggaca ccttgggtgg ttcgtttcca tccattgtac    480
cctgaaatac tggcaagtgg aagtttggac cacgaagttc ggctgtggga tgcaaaaact    540
gccgagtgta taggatcgcg agatttttat cgccccatcg catccatagc gttccatgcc    600
```

```
caaggggaag ttctagccgt tgcttcaggc cacaagcttt atatatggca ttacaacaga      660
agaggagagg cttctacacc agcaattgta ctgaagacac ggcgttctct tcgtgctgtc      720
catttccacc cacatgctac cccatttctt ttgacagctg aggtcaatga tctggattca      780
tcagattctt caatgacacg tgctacttct ccggcaaatg aactgcctat catgtctcta      840
cctttcctga tctggccgtc aattgcaaga ggtgatccca gaatgactgt gcagcaaact      900
gatatagata tggtaaccga caatgtacag cacagaacag atacttcatc atctgtccgc      960
cttctcacat attcaactcc gtccggccag tatgaacttt tattgtcccc tgttgagcaa     1020
agtgcatctc ccgcacaaga agctcatact ggttcttctg ttggggagaa tgagaatata     1080
ggatggttga ttggccaaag ccaagttgcc caacaagcaa ctcatccaga ccttagtggt     1140
actaccacta atccatcaac ttatgatgaa ctggaaaatc cttctgctgt tccgttggta     1200
atttcaagca atactcatcc aaggtccgga agatctggtt ctcggcaacg ttcttcacgc     1260
tctcgagcga ttcctgttgc tggagctggt gctggtgctg cttcgcttaa cgttatgcat     1320
gatgagagtg attctcaaac ttctattggt cgcatccagt cggagatagc tacttcactg     1380
gctgcagcag cggctgctga attgccttgc actgtgaaac tcagaatatg gcctcatgat     1440
gttaaggttc catgtgcacc ccttcatgct gaaagatgtc gcttaacaat accacatgct     1500
gtactttgca gtgaaatggg agcccatttt tcaccatgtg ggagattttt agcagcttgt     1560
gttgcatgta ttctgccaaa cgtggatgct gatcctggtt ttcatggcca tcttcatcat     1620
gatactatgg cagctggaac ttctccaacc agacatccag ttgctgccca ccaggttatg     1680
tatgagctac ggatatattc cctggaggag gcaacgtttg gttcagtgct tgcatctcga     1740
gcaattagag ctgctcattg tttgacttca attcagtttt ctccggcttc agagcatctg     1800
ttacttgctt atgggcgtcg ccatagttca ctacttaaaa gtgttgttat tgatggagac     1860
acaactatac ccatttacac tattcttgag gtctatagag tttctgatat ggaacttgtg     1920
agagttctcc ccagtgcgga ggatgaggtt aatgtcgctt gcttccatcc ttcggttggt     1980
ggtggccttg tctatggaac caaggaaggg aagttgagga ttctccaata tgacaattca     2040
aatggtttgg gtcgcacaat atcctgttct cctgtcgaaa acattgtcga ggtattataa     2100
```

<210> SEQ ID NO 5
<211> LENGTH: 2238
<212> TYPE: DNA
<213> ORGANISM: Artificial Sequence
<220> FEATURE:
<223> OTHER INFORMATION: NbRTP5-3

<400> SEQUENCE: 5

```
atgagggcgt cactttggcc ggagaattca agcagcgatt catccacgtc aattttgcgg       60
cggcggaatt cgccgcctca ttcgattgcc caaaaccta attgtaaaca tagctgcggt      120
aacgtctttc agctgctaac gaggagggag gtatctcctc gaactaaacg cagttctaag      180
aagttttggg gtgagaactc taaatgttct gttcattcct gtggattaaa aagccaagta      240
gcaagagacc cgaggcaggg tcttatatca tgggtagagg cagagtcatt gagacatttt      300
tcagctaagt attgtccact gttgcgtccg cctaggtcta ctattgctgc ggcattcagt      360
cctgatggga agacactcgc ttctactcat ggagatcaca cagtaaagat aattgattgc      420
caaagtggaa agtgcttaaa ggtgttaagt ggacatcgca ggactccttg ggtggttcgt      480
ttccatccat tatactctga tatacttgca agtggaagtt tggaccatga agttcgttta      540
```

```
tgggatgcaa aaactgccga gtgtatagga tcacgtgatt tttatcgtcc tattgcatcc    600
attgccttcc atgcccaagg ggaagttctg gctgttgctt caggccacaa gctgtatatg    660
tggcactaca acagaagagg ggaagcatct tcaccagcta tcgtactaaa gacaagacgt    720
tcacttcgtg ctgtacattt ccacccacat ggtgccccat ttcttttaac agctgaggtc    780
aatgatctgg actcatcaga ttcttcaatg acgcttgcaa cttctccggc aaatgaattg    840
ccgatcatgt ctctaccatt catgatctgg ccttcaatcg ctagaggtga tcctagaatg    900
cctttgcagc tgagcgatgc agacatggct tctgacagca cacagcagag agccgacact    960
tctgcatctg tccgacttct cacttactca actccttctg ccaatatga acttttattg   1020 tcccctgttg agccaacttt atctcctgca caagctcaga ctggttcttc tgttagggat   1080
actgagaatg catccgaacc tgtagttgat cctatggaga ctgatgtgcc ggctgaggaa   1140
agaaacaatc aattttttccc tttcagtgac cctgcatatt gggaattacc tttcttgcaa   1200
ggatggttga ttggccaaag ccaagctggc agacgagcga ttcattcaga gcacagtggt   1260
gccactagta gtgtatcggc ttatggtgaa gtagaacatc ctcctgcagt tccgtcagtc   1320
atttcaaaca gtaatcatcc aaggtctgaa agatctggct ctcgtcaccg ttcttcacgc   1380
tctagagcga tacctgttgt tggatctggt gatagcgctg ctcccattaa cattgtacat   1440
gatgaaaatg attctcatgc ttttatgagt cggttccagt cagagatagc tacttcactg   1500
gctgcagcag ctgctcccga attgccttgc actgtgaaac tcagaatttg gccttatgat   1560
gttaaggctc catgtgcacc gcttgaagct gaaaattgtc gtttaatgat accacatgct   1620
gtgctttgta gtgaaatggg agcccacttt tcaccatgtg ggaggttttt agccgcttgt   1680
gttgcatgta ttctgcctaa catggaagct gatcctggtt ttcaaggaca acttcaccat   1740
gatgccatgg gtgctgcaac ttcacctacc agacatccta ttgcagccca tcgggttatg   1800
tatgagctac gaatatattc cttggaggag gcgacgtttg gtttagtgct tgtatctcgg   1860
gcaattagag ctgcacattg tttgacttca attcagtttt ctccaacttc tgaacatctt   1920
ttacttgcct atgggcgtcg gcacggttca cttctgaaaa gtatagtgat tgatggagat   1980
acaactgttc ctgtttacac gattcttgag gtctacagag tttcagatat ggaacttgtg   2040
agagttcttc ccagtgcaga ggatgaggtt aatgttgctt gtttccatcc tttggttggt   2100
ggcggcctag tctatggaac caaggaagga aaattgagga tcctccaatt tgataaatca   2160
aatggtttgg accgtacagt atcctgtttt cctgatgaag acatgctgga ggttccaaca   2220
tatgctttag aaggctag                                                 2238

<210> SEQ ID NO 6
<211> LENGTH: 978
<212> TYPE: DNA
<213> ORGANISM: Artificial Sequence
<220> FEATURE:
<223> OTHER INFORMATION: NbRTP5-4

<400> SEQUENCE: 6
atggagactg atgtgcagcc agaagaaaga aacaatcagt tttttccctt tagtgaccca     60
gcatactggg aattgccttt tttgcaagga tggttgattg ccaaagcca agttgcccaa    120 caaggaactc atccagacct tagtgatact accactaatc catcaactta tggtgaactg    180
gaaaatcctt ctgctgttcc cttggcaatt tcaagcaata atcgtccaag gtccggaaga    240
tctggttctc ggcaacgttc ttcacgctct cgagcgattc ctgttgctgg aggtggtgct    300
tcttcgctta acttttatgca tgatgagagt gattctcaaa cttcgattgc tcgcatccag    360
```

```
tcagagatag ctacttcgct ggctgcagca gcggctgctg aattgccttg cactgtgaaa    420
ctcagaatat ggcctcatga tgttaaggtt ccatgtgcac cccttcatgc tgaaagatgt    480
cgcttaacaa taccacatgc tgtactttgc agtgaaatgg gagcccattt ttcaccatgt    540
gggagattct tagcaacttg tgttgcatgt attctgccaa acgtggatgc tgatcctagt    600
tttcatggcc atcttcatca tgatactatg gcagctggaa cttctccaac cagacatcca    660
gttgctgccc accaggttat gtatgagcta cggatatatt ccctggagga ggcagcgttt    720
ggttcagtgc ttgcatctcg agcaattaga gctgctcatt gtttaacttc aattcaggtc    780
tatagagttt ctgatatgga acttgtgaga gttctcccca gtgcggagga tgaggttaat    840
gtcgcttgct ccatccttc ggttggtggt ggccttgtct atggaaccaa ggaagggaag    900
ttgaggattc tccaatatga caattcaaat tggcaaaaag aaattagctc caaatttcca    960
ataactgtat tcttctga                                                 978
```

<210> SEQ ID NO 7
<211> LENGTH: 769
<212> TYPE: PRT
<213> ORGANISM: Artificial Sequence
<220> FEATURE:
<223> OTHER INFORMATION: the amino acid sequence of NbRTP5-1

<400> SEQUENCE: 7

```
Met Arg Ala Ser Leu Trp Pro Glu Asn Ser Ser Asp Ser Ser Thr
1               5                   10                  15

Ser Ile Ser Arg Arg Asn Ser Pro Pro His Ser Ile Ser Gln Asn
                20                  25                  30

Pro Asn Cys Lys His Ser Cys Gly Asn Val Phe Gln Leu Leu Thr Arg
            35                  40                  45

Arg Glu Val Ser Pro Arg Thr Lys Arg Ser Ser Thr Lys Phe Trp Gly
        50                  55                  60

Glu Asn Ser Lys Cys Ser Val Tyr Ser Cys Gly Leu Lys Ser Gln Val
65                  70                  75                  80

Ala Arg Asp Pro Arg Gln Gly Leu Ile Ser Trp Val Glu Ala Glu Ser
                85                  90                  95

Leu Arg His Phe Ser Ala Lys Tyr Cys Pro Leu Leu Pro Pro Arg
            100                 105                 110

Ser Thr Ile Ala Ala Ala Phe Ser Pro Asp Gly Lys Thr Leu Ala Ser
        115                 120                 125

Thr His Gly Asp His Thr Val Lys Ile Ile Asp Cys Gln Ser Gly Lys
    130                 135                 140

Cys Leu Lys Val Leu Ser Gly His Arg Arg Thr Pro Trp Val Val Arg
145                 150                 155                 160

Phe His Pro Leu Tyr Ser Asp Ile Leu Ala Ser Gly Ser Leu Asp His
                165                 170                 175

Glu Val Arg Leu Trp Asp Ala Lys Thr Ala Glu Cys Ile Gly Ser His
            180                 185                 190

Arg Pro Ile Ala Ser Ile Ala Phe His Ala Gln Gly Glu Val Leu Ala
        195                 200                 205

Val Ala Ser Gly His Lys Leu Tyr Met Trp His Tyr Asn Arg Arg Gly
    210                 215                 220

Glu Ala Ser Ser Pro Ala Ile Val Leu Lys Thr Arg Arg Ser Leu Arg
225                 230                 235                 240

Ala Val His Phe His Pro His Gly Ala Pro Phe Leu Leu Thr Ala Glu
```

```
              245                 250                 255
Val Asn Asp Leu Asp Ser Ser Asp Ser Ser Met Thr Leu Ala Thr Ser
            260                 265                 270

Pro Gly Asn Leu Arg Tyr Pro Pro Thr Val Tyr Leu Thr Asp Ala
            275                 280                 285

His Ser Thr Tyr Arg Ser Ala Ser Asn Glu Leu Pro Ile Met Ser
            290                 295                 300

Leu Pro Phe Met Ile Trp Pro Ser Ile Ala Arg Gly Asp Pro Gly Met
305                 310                 315                 320

Pro Leu Gln Gln Ser Asp Ala Asp Met Ala Ser Asp Ser Thr Gln His
                325                 330                 335

Arg Ala Asp Thr Tyr Ala Ser Val Arg Leu Leu Thr Tyr Ser Thr Pro
                340                 345                 350

Ser Gly Gln Tyr Glu Leu Leu Leu Ser Pro Val Glu Pro Thr Leu Ser
                355                 360                 365

Pro Ala Gln Ala Gln Thr Gly Ser Ser Val Arg Asn Ile Glu Asn Ala
370                 375                 380

Ser Glu Pro Val Val Asp Pro Met Asp Thr Asp Val Pro Ala Glu Glu
385                 390                 395                 400

Arg Asn Asn Gln Phe Phe Pro Phe Ser Asp Pro Ala Tyr Trp Glu Leu
                405                 410                 415

Pro Phe Leu Gln Gly Trp Leu Ile Gly Gln Ser Gln Ala Gly Arg Arg
                420                 425                 430

Ala Ile His Ser Glu His Ser Gly Ala Thr Ser Ser Val Ser Ala Tyr
                435                 440                 445

Gly Glu Val Glu His Pro Pro Ala Val Pro Ser Val Ile Ser Asn Ser
            450                 455                 460

Asn His Ser Arg Ser Gly Arg Ser Gly Ser Arg His Arg Ser Ser Arg
465                 470                 475                 480

Ser Arg Ala Ile Pro Val Val Gly Ser Gly Asp Ser Ala Ala Pro Ile
                485                 490                 495

Asn Val Val His Asp Glu Asn Asp Ser Gln Ala Phe Met Ser Gln Phe
            500                 505                 510

Gln Ser Glu Ile Ala Thr Ser Leu Ala Ala Ala Ala Pro Glu Leu
    515                 520                 525

Pro Cys Thr Val Lys Leu Arg Ile Trp Pro Tyr Asp Val Lys Ala Pro
            530                 535                 540

Cys Ala Pro Leu Asp Ala Glu Asn Cys Arg Leu Met Ile Pro His Ala
545                 550                 555                 560

Val Leu Cys Ser Glu Met Gly Ala His Phe Ser Pro Cys Gly Arg Phe
                565                 570                 575

Leu Ala Ala Cys Val Ala Cys Ile Leu Pro Asn Met Glu Ala Glu Pro
                580                 585                 590

Gly Phe His Gly Gln Leu His His Asp Ala Met Gly Ala Ala Thr Ser
                595                 600                 605

Pro Thr Arg His Pro Ile Ala Ala His Arg Val Met Tyr Glu Leu Arg
            610                 615                 620

Ile Tyr Ser Leu Glu Glu Ala Thr Phe Gly Leu Val Leu Val Ser Arg
625                 630                 635                 640

Ala Ile Arg Ala Ala His Cys Leu Thr Ser Ile Gln Phe Ser Pro Thr
                645                 650                 655

Ser Glu His Leu Leu Leu Ala Tyr Gly Arg Arg His Gly Ser Leu Leu
                660                 665                 670
```

```
Lys Ser Ile Val Val Asp Gly Asp Thr Thr Val Pro Val Tyr Thr Ile
            675                 680                 685

Leu Glu Val Tyr Arg Val Ser Asp Met Glu Leu Val Arg Val Leu Pro
        690                 695                 700

Ser Ala Glu Asp Glu Val Asn Val Ala Cys Phe His Pro Leu Val Gly
705                 710                 715                 720

Gly Gly Leu Val Tyr Gly Thr Lys Glu Gly Lys Leu Arg Ile Leu Gln
                725                 730                 735

Phe Asp Lys Ser Asn Gly Cys His Glu Asn Ile Arg Ile Arg Thr Met
            740                 745                 750

Thr Gly Gly Cys Lys Val Glu Cys Val Ala Asp Gly Asp Cys Ile Val
            755                 760                 765

Ser

<210> SEQ ID NO 8
<211> LENGTH: 699
<212> TYPE: PRT
<213> ORGANISM: Artificial Sequence
<220> FEATURE:
<223> OTHER INFORMATION: the amino acid sequence of NbRTP5-2

<400> SEQUENCE: 8

Met Arg Ser Ser Val Leu Pro Glu Asn Ser Gly Ser Ala Pro Ser Thr
1               5                   10                  15

Ser Arg Asn Ser Pro Pro Ser Ala Thr Ala Pro Arg Asn Ser Asn Cys
            20                  25                  30

Lys His Ser Asn Val Phe Gln Leu Leu Thr Arg Arg Glu Val Ser Ser
        35                  40                  45

Arg Thr Lys Arg Ala Ser Arg Lys Phe Trp Gly Glu Asn Thr Lys Cys
    50                  55                  60

Thr Leu Asp Ser Cys Gly Leu Lys Ser Glu Val Ala Ser Asp Ala Arg
65                  70                  75                  80

Arg Gly Leu Ile Ser Trp Val Glu Ala Glu Ser Leu Gln His Leu Ser
                85                  90                  95

Ala Lys Tyr Cys Ser Leu Leu Pro Pro Arg Ser Thr Ile Ala Ala
            100                 105                 110

Ala Phe Ser Pro Asp Gly Arg Thr Leu Ala Ser Thr His Gly Asp His
        115                 120                 125

Thr Val Lys Ile Ile Asp Cys Gln Thr Gly Lys Cys Leu Lys Val Leu
    130                 135                 140

Ser Gly His Arg Arg Thr Pro Trp Val Val Arg Phe His Pro Leu Tyr
145                 150                 155                 160

Pro Glu Ile Leu Ala Ser Gly Ser Leu Asp His Glu Val Arg Leu Trp
                165                 170                 175

Asp Ala Lys Thr Ala Glu Cys Ile Gly Ser Arg Asp Phe Tyr Arg Pro
            180                 185                 190

Ile Ala Ser Ile Ala Phe His Ala Gln Gly Glu Val Leu Ala Val Ala
        195                 200                 205

Ser Gly His Lys Leu Tyr Ile Trp His Tyr Asn Arg Arg Gly Glu Ala
    210                 215                 220

Ser Thr Pro Ala Ile Val Leu Lys Thr Arg Arg Ser Leu Arg Ala Val
225                 230                 235                 240

His Phe His Pro His Ala Thr Pro Phe Leu Leu Thr Ala Glu Val Asn
                245                 250                 255
```

-continued

Asp Leu Asp Ser Ser Asp Ser Ser Met Thr Arg Ala Thr Ser Pro Ala
            260                 265                 270

Asn Glu Leu Pro Ile Met Ser Leu Pro Phe Leu Ile Trp Pro Ser Ile
            275                 280                 285

Ala Arg Gly Asp Pro Arg Met Thr Val Gln Gln Thr Asp Ile Asp Met
290                 295                 300

Val Thr Asp Asn Val Gln His Arg Thr Asp Thr Ser Ser Ser Val Arg
305                 310                 315                 320

Leu Leu Thr Tyr Ser Thr Pro Ser Gly Gln Tyr Glu Leu Leu Leu Ser
                325                 330                 335

Pro Val Glu Gln Ser Ala Ser Pro Ala Gln Glu Ala His Thr Gly Ser
            340                 345                 350

Ser Val Gly Glu Asn Glu Asn Ile Gly Trp Leu Ile Gly Gln Ser Gln
            355                 360                 365

Val Ala Gln Gln Ala Thr His Pro Asp Leu Ser Gly Thr Thr Thr Asn
            370                 375                 380

Pro Ser Thr Tyr Asp Glu Leu Glu Asn Pro Ser Ala Val Pro Leu Val
385                 390                 395                 400

Ile Ser Ser Asn Thr His Pro Arg Ser Gly Arg Ser Gly Ser Arg Gln
                405                 410                 415

Arg Ser Ser Arg Ser Arg Ala Ile Pro Val Ala Gly Ala Gly Ala Gly
            420                 425                 430

Ala Ala Ser Leu Asn Val Met His Asp Glu Ser Asp Ser Gln Thr Ser
            435                 440                 445

Ile Gly Arg Ile Gln Ser Glu Ile Ala Thr Ser Leu Ala Ala Ala Ala
450                 455                 460

Ala Ala Glu Leu Pro Cys Thr Val Lys Leu Arg Ile Trp Pro His Asp
465                 470                 475                 480

Val Lys Val Pro Cys Ala Pro Leu His Ala Glu Arg Cys Arg Leu Thr
                485                 490                 495

Ile Pro His Ala Val Leu Cys Ser Glu Met Gly Ala His Phe Ser Pro
            500                 505                 510

Cys Gly Arg Phe Leu Ala Ala Cys Val Ala Cys Ile Leu Pro Asn Val
            515                 520                 525

Asp Ala Asp Pro Gly Phe His Gly His Leu His His Asp Thr Met Ala
530                 535                 540

Ala Gly Thr Ser Pro Thr Arg His Pro Val Ala Ala His Gln Val Met
545                 550                 555                 560

Tyr Glu Leu Arg Ile Tyr Ser Leu Glu Glu Ala Thr Phe Gly Ser Val
                565                 570                 575

Leu Ala Ser Arg Ala Ile Arg Ala Ala His Cys Leu Thr Ser Ile Gln
            580                 585                 590

Phe Ser Pro Ala Ser Glu His Leu Leu Leu Ala Tyr Gly Arg Arg His
            595                 600                 605

Ser Ser Leu Leu Lys Ser Val Val Ile Asp Gly Asp Thr Thr Ile Pro
610                 615                 620

Ile Tyr Thr Ile Leu Glu Val Tyr Arg Val Ser Asp Met Glu Leu Val
625                 630                 635                 640

Arg Val Leu Pro Ser Ala Glu Asp Glu Val Asn Val Ala Cys Phe His
                645                 650                 655

Pro Ser Val Gly Gly Leu Val Tyr Gly Thr Lys Glu Gly Lys Leu
            660                 665                 670

Arg Ile Leu Gln Tyr Asp Asn Ser Asn Gly Leu Gly Arg Thr Ile Ser

```
            675                 680                 685
Cys Ser Pro Val Glu Asn Ile Val Glu Val Leu
    690                 695

<210> SEQ ID NO 9
<211> LENGTH: 745
<212> TYPE: PRT
<213> ORGANISM: Artificial Sequence
<220> FEATURE:
<223> OTHER INFORMATION: the amino acid sequence of NbRTP5-3

<400> SEQUENCE: 9

Met Arg Ala Ser Leu Trp Pro Glu Asn Ser Ser Asp Ser Ser Thr
1               5                   10                  15

Ser Ile Leu Arg Arg Arg Asn Ser Pro Pro His Ser Ile Ala Gln Asn
                20                  25                  30

Pro Asn Cys Lys His Ser Cys Gly Asn Val Phe Gln Leu Leu Thr Arg
            35                  40                  45

Arg Glu Val Ser Pro Arg Thr Lys Arg Ser Ser Lys Lys Phe Trp Gly
    50                  55                  60

Glu Asn Ser Lys Cys Ser Val His Ser Cys Gly Leu Lys Ser Gln Val
65                  70                  75                  80

Ala Arg Asp Pro Arg Gln Gly Leu Ile Ser Trp Val Glu Ala Glu Ser
                85                  90                  95

Leu Arg His Phe Ser Ala Lys Tyr Cys Pro Leu Leu Arg Pro Pro Arg
            100                 105                 110

Ser Thr Ile Ala Ala Phe Ser Pro Asp Gly Lys Thr Leu Ala Ser
        115                 120                 125

Thr His Gly Asp His Thr Val Lys Ile Ile Asp Cys Gln Ser Gly Lys
    130                 135                 140

Cys Leu Lys Val Leu Ser Gly His Arg Arg Thr Pro Trp Val Val Arg
145                 150                 155                 160

Phe His Pro Leu Tyr Ser Asp Ile Leu Ala Ser Gly Ser Leu Asp His
                165                 170                 175

Glu Val Arg Leu Trp Asp Ala Lys Thr Ala Glu Cys Ile Gly Ser Arg
            180                 185                 190

Asp Phe Tyr Arg Pro Ile Ala Ser Ile Ala Phe His Ala Gln Gly Glu
        195                 200                 205

Val Leu Ala Val Ala Ser Gly His Lys Leu Tyr Met Trp His Tyr Asn
    210                 215                 220

Arg Arg Gly Glu Ala Ser Ser Pro Ala Ile Val Leu Lys Thr Arg Arg
225                 230                 235                 240

Ser Leu Arg Ala Val His Phe His Pro His Gly Ala Pro Phe Leu Leu
                245                 250                 255

Thr Ala Glu Val Asn Asp Leu Asp Ser Ser Asp Ser Ser Met Thr Leu
            260                 265                 270

Ala Thr Ser Pro Ala Asn Glu Leu Pro Ile Met Ser Leu Pro Phe Met
        275                 280                 285

Ile Trp Pro Ser Ile Ala Arg Gly Asp Pro Arg Met Pro Leu Gln Leu
    290                 295                 300

Ser Asp Ala Asp Met Ala Ser Asp Ser Thr Gln Gln Arg Ala Asp Thr
305                 310                 315                 320

Ser Ala Ser Val Arg Leu Leu Thr Tyr Ser Thr Pro Ser Gly Gln Tyr
                325                 330                 335

Glu Leu Leu Leu Ser Pro Val Glu Pro Thr Leu Ser Pro Ala Gln Ala
```

```
                    340                 345                 350
Gln Thr Gly Ser Ser Val Arg Asp Thr Glu Asn Ala Ser Glu Pro Val
            355                 360                 365

Val Asp Pro Met Glu Thr Asp Val Pro Ala Glu Arg Asn Asn Gln
370                 375                 380

Phe Phe Pro Phe Ser Asp Pro Ala Tyr Trp Glu Leu Pro Phe Leu Gln
385                 390                 395                 400

Gly Trp Leu Ile Gly Gln Ser Gln Ala Gly Arg Arg Ala Ile His Ser
                405                 410                 415

Glu His Ser Gly Ala Thr Ser Ser Val Ser Ala Tyr Gly Glu Val Glu
            420                 425                 430

His Pro Pro Ala Val Pro Ser Val Ile Ser Asn Ser Asn His Pro Arg
            435                 440                 445

Ser Glu Arg Ser Gly Ser Arg His Arg Ser Ser Arg Ser Arg Ala Ile
        450                 455                 460

Pro Val Val Gly Ser Gly Asp Ser Ala Ala Pro Ile Asn Ile Val His
465                 470                 475                 480

Asp Glu Asn Asp Ser His Ala Phe Met Ser Arg Phe Gln Ser Glu Ile
                485                 490                 495

Ala Thr Ser Leu Ala Ala Ala Ala Pro Glu Leu Pro Cys Thr Val
            500                 505                 510

Lys Leu Arg Ile Trp Pro Tyr Asp Val Lys Ala Pro Cys Ala Pro Leu
            515                 520                 525

Glu Ala Glu Asn Cys Arg Leu Met Ile Pro His Ala Val Leu Cys Ser
    530                 535                 540

Glu Met Gly Ala His Phe Ser Pro Cys Gly Arg Phe Leu Ala Ala Cys
545                 550                 555                 560

Val Ala Cys Ile Leu Pro Asn Met Glu Ala Asp Pro Gly Phe Gln Gly
                565                 570                 575

Gln Leu His His Asp Ala Met Gly Ala Ala Thr Ser Pro Thr Arg His
            580                 585                 590

Pro Ile Ala Ala His Arg Val Met Tyr Glu Leu Arg Ile Tyr Ser Leu
            595                 600                 605

Glu Glu Ala Thr Phe Gly Leu Val Leu Val Ser Arg Ala Ile Arg Ala
    610                 615                 620

Ala His Cys Leu Thr Ser Ile Gln Phe Ser Pro Thr Ser Glu His Leu
625                 630                 635                 640

Leu Leu Ala Tyr Gly Arg Arg His Gly Ser Leu Leu Lys Ser Ile Val
                645                 650                 655

Ile Asp Gly Asp Thr Thr Val Pro Val Tyr Thr Ile Leu Glu Val Tyr
            660                 665                 670

Arg Val Ser Asp Met Glu Leu Val Arg Val Leu Pro Ser Ala Glu Asp
            675                 680                 685

Glu Val Asn Val Ala Cys Phe His Pro Leu Val Gly Gly Leu Val
    690                 695                 700

Tyr Gly Thr Lys Glu Gly Lys Leu Arg Ile Leu Gln Phe Asp Lys Ser
705                 710                 715                 720

Asn Gly Leu Asp Arg Thr Val Ser Cys Phe Pro Asp Glu Asp Met Leu
                725                 730                 735

Glu Val Pro Thr Tyr Ala Leu Glu Gly
            740                 745

<210> SEQ ID NO 10
```

<211> LENGTH: 325
<212> TYPE: PRT
<213> ORGANISM: Artificial Sequence
<220> FEATURE:
<223> OTHER INFORMATION: the amino acid sequence of NbRTP5-4

<400> SEQUENCE: 10

```
Met Glu Thr Asp Val Gln Pro Glu Glu Arg Asn Asn Gln Phe Phe Pro
1               5                   10                  15

Phe Ser Asp Pro Ala Tyr Trp Glu Leu Pro Phe Leu Gly Trp Leu
            20                  25                  30

Ile Gly Gln Ser Gln Val Ala Gln Gln Gly Thr His Pro Asp Leu Ser
                35                  40                  45

Asp Thr Thr Thr Asn Pro Ser Thr Tyr Gly Glu Leu Glu Asn Pro Ser
    50                  55                  60

Ala Val Pro Leu Ala Ile Ser Ser Asn Asn Arg Pro Arg Ser Gly Arg
65                  70                  75                  80

Ser Gly Ser Arg Gln Arg Ser Ser Arg Ser Arg Ala Ile Pro Val Ala
                85                  90                  95

Gly Gly Gly Ala Ser Ser Leu Asn Phe Met His Asp Glu Ser Asp Ser
            100                 105                 110

Gln Thr Ser Ile Ala Arg Ile Gln Ser Glu Ile Ala Thr Ser Leu Ala
        115                 120                 125

Ala Ala Ala Ala Glu Leu Pro Cys Thr Val Lys Leu Arg Ile Trp
130                 135                 140

Pro His Asp Val Lys Val Pro Cys Ala Pro Leu His Ala Glu Arg Cys
145                 150                 155                 160

Arg Leu Thr Ile Pro His Ala Val Leu Cys Ser Glu Met Gly Ala His
                165                 170                 175

Phe Ser Pro Cys Gly Arg Phe Leu Ala Thr Cys Val Ala Cys Ile Leu
            180                 185                 190

Pro Asn Val Asp Ala Asp Pro Ser Phe His Gly His Leu His His Asp
        195                 200                 205

Thr Met Ala Ala Gly Thr Ser Pro Thr Arg His Pro Val Ala Ala His
    210                 215                 220

Gln Val Met Tyr Glu Leu Arg Ile Tyr Ser Leu Glu Glu Ala Ala Phe
225                 230                 235                 240

Gly Ser Val Leu Ala Ser Arg Ala Ile Arg Ala Ala His Cys Leu Thr
                245                 250                 255

Ser Ile Gln Val Tyr Arg Val Ser Asp Met Glu Leu Val Arg Val Leu
            260                 265                 270

Pro Ser Ala Glu Asp Glu Val Asn Val Ala Cys Phe His Pro Ser Val
        275                 280                 285

Gly Gly Gly Leu Val Tyr Gly Thr Lys Glu Gly Lys Leu Arg Ile Leu
    290                 295                 300

Gln Tyr Asp Asn Ser Asn Trp Gln Lys Glu Ile Ser Ser Lys Phe Pro
305                 310                 315                 320

Ile Thr Val Phe Phe
                325
```

<210> SEQ ID NO 11
<211> LENGTH: 32
<212> TYPE: DNA
<213> ORGANISM: Artificial Sequence
<220> FEATURE:
<223> OTHER INFORMATION: AtRTP5-F

<400> SEQUENCE: 11
ccggaattca tgactcaatc tatctgttcg tc                                32

<210> SEQ ID NO 12
<211> LENGTH: 29
<212> TYPE: DNA
<213> ORGANISM: Artificial Sequence
<220> FEATURE:
<223> OTHER INFORMATION: AtRTP5-R

<400> SEQUENCE: 12
gcgcggatcc ttaggtgttt ggtcctgtg                                    29

<210> SEQ ID NO 13
<211> LENGTH: 20
<212> TYPE: DNA
<213> ORGANISM: Artificial Sequence
<220> FEATURE:
<223> OTHER INFORMATION: pKAN-F

<400> SEQUENCE: 13
caatcccact atccttcgca                                              20

<210> SEQ ID NO 14
<211> LENGTH: 20
<212> TYPE: DNA
<213> ORGANISM: Artificial Sequence
<220> FEATURE:
<223> OTHER INFORMATION: pKAN-R

<400> SEQUENCE: 14
cggtaaggat ctgagctaca                                              20

<210> SEQ ID NO 15
<211> LENGTH: 400
<212> TYPE: DNA
<213> ORGANISM: Artificial Sequence
<220> FEATURE:
<223> OTHER INFORMATION: target sequence

<400> SEQUENCE: 15
tgcatctgtc cgacttctca cttactcaac tccttctggc caatatgaac ttttgttgtc    60
ccctgttgag ccaactttat ctcctgcaca agctcagact ggttcttctg ttaggaatat   120
tgagaatgca tccgaacctg tagttgatcc tatggatact gatgtgccgg ctgaggaaag   180
aaacaatcaa ttttccctt gaaaattttg gggtgagaac actaaatgta ctcttgactc    240
ctgtggatta aaaagtgaag tggcaagtga tgctagacgg ggactaatat catgggtaga   300
ggcggagtca ctgcaacatt tatcggccaa gtattgttca ctgttgcctc ctccaaggtc   360
taccattgca gcagcattca gtcctgatgg gaggacactt                         400

<210> SEQ ID NO 16
<211> LENGTH: 39
<212> TYPE: DNA
<213> ORGANISM: Artificial Sequence
<220> FEATURE:
<223> OTHER INFORMATION: tNbRTP5-1F

<400> SEQUENCE: 16
gttaccgaat tctctagatg catctgtccg acttctcac                         39

<210> SEQ ID NO 17
<211> LENGTH: 36

-continued

```
<212> TYPE: DNA
<213> ORGANISM: Artificial Sequence
<220> FEATURE:
<223> OTHER INFORMATION: tNbRTP5-1R

<400> SEQUENCE: 17
caaaattttc aagggaaaaa ttgattgttt ctttcc                                    36

<210> SEQ ID NO 18
<211> LENGTH: 33
<212> TYPE: DNA
<213> ORGANISM: Artificial Sequence
<220> FEATURE:
<223> OTHER INFORMATION: tNbRTP5-2F

<400> SEQUENCE: 18 tttttcccttt gaaaattttg gggtgagaac act                                     33

<210> SEQ ID NO 19
<211> LENGTH: 39
<212> TYPE: DNA
<213> ORGANISM: Artificial Sequence
<220> FEATURE:
<223> OTHER INFORMATION: tNbRTP5-2R

<400> SEQUENCE: 19
gagctcggta ccggatccaa gtgtcctccc atcaggact                                39

<210> SEQ ID NO 20
<211> LENGTH: 776
<212> TYPE: PRT
<213> ORGANISM: Artificial Sequence
<220> FEATURE:
<223> OTHER INFORMATION: the amino acid sequence of XP_006340895.1

<400> SEQUENCE: 20
```

Met Arg Gly Ser Leu Trp Pro Glu Asn Ser Ser Asp Ser Ser Thr
1               5                   10                  15

Ser Asn Pro Ile His Val Pro Leu Pro Pro Pro Pro Gly Trp Asn
            20                  25                  30

Ser Pro Ser Leu Pro Ile Glu Gln Asn Pro Asn Cys Lys Asn Arg Cys
        35                  40                  45

Gly Asn Val Phe Gln Leu Leu Thr Arg Glu Val Ser Pro Arg Ala
    50                  55                  60

Lys Arg Ser Ser Lys Lys Leu Trp Asp Glu Asn Ser Lys Tyr Cys Ala
65                  70                  75                  80

His Ser Tyr Glu Lys Leu Lys Ser Gln Val Ala Arg Asp Pro Arg Arg
                85                  90                  95

Gly Leu Ile Ser Trp Val Glu Ala Glu Ser Leu Arg His Phe Ser Ala
            100                 105                 110

Lys Tyr Cys Pro Leu Leu Pro Pro Arg Ser Thr Ile Ala Ala Ala
        115                 120                 125

Phe Ser Pro Asp Gly Lys Thr Leu Ala Ser Thr His Gly Asp His Thr
    130                 135                 140

Val Lys Ile Ile Asp Cys Gln Ser Gly Lys Cys Leu Lys Val Leu Ser
145                 150                 155                 160

Gly His Arg Arg Thr Pro Trp Val Val Arg Phe His Pro Leu His Ser
                165                 170                 175

Glu Ile Leu Ala Ser Gly Ser Leu Asp His Glu Val Arg Leu Trp Asp
            180                 185                 190

```
Ala Lys Thr Ala Glu Cys Ile Gly Ser Arg Asp Phe Tyr Arg Pro Ile
        195                 200                 205

Ala Ser Ile Ala Phe His Ala Gln Gly Glu Val Leu Ala Val Ala Ser
    210                 215                 220

Gly His Lys Leu Tyr Met Trp His Tyr Asn Arg Arg Glu Glu Ala Ser
225                 230                 235                 240

Ser Pro Ala Ile Ile Leu Lys Thr Arg Arg Ser Leu Arg Ala Val His
                245                 250                 255

Phe His Pro His Gly Ala Pro Tyr Leu Thr Ala Glu Val Asn Asp
            260                 265                 270

Leu Asp Ser Ser Asp Pro Leu Met Thr Phe Ala Thr Ser Leu Gly Asn
        275                 280                 285

Leu Arg Tyr Pro Pro Thr Val Tyr Leu Thr Asp Ala His Ser Thr
    290                 295                 300

Tyr Arg Ser Ala Ser Ala Asn Glu Leu Pro Ile Met Ser Leu Pro Ile
305                 310                 315                 320

Met Ile Trp Pro Ser Ile Ala Arg Gly Asp Pro Arg Met Pro Leu Gln
                325                 330                 335

Gln Ser Asn Val Asp Met Gly Ser Asp Ser Thr Gln Asn Arg Ala Asp
        340                 345                 350

Thr Ser Ala Ser Val Arg Leu Leu Thr Tyr Ser Thr Pro Ser Gly Gln
    355                 360                 365

Tyr Glu Leu Leu Leu Ser Pro Val Glu Pro Thr Leu Ser Pro Ala Gln
370                 375                 380

Glu Ala Gln Thr Ser Ser Ser Val Arg Asp Thr Glu Asn Ala Ser Asn
385                 390                 395                 400

Pro Val Val Asp Pro Met Glu Thr Asp Val Pro Thr Glu Glu Arg Asn
                405                 410                 415

Asn Gln Phe Phe Pro Phe Ser Asp Pro Ala Tyr Trp Asp Leu Pro Phe
        420                 425                 430

Leu Gln Gly Trp Leu Ile Gly Gln Ser Gln Ala Gly Arg Arg Ser Ile
    435                 440                 445

His Ser Glu His Ser Gly Ala Thr Asn Ile Val Ser Ala Tyr Gly Glu
450                 455                 460

Val Glu His Pro Pro Ala Val Pro Ser Ile Ile Ser Asn Ser Asn His
465                 470                 475                 480

Pro Arg Ser Gly Arg Ser Gly Ser Arg His Arg Ser Ser Arg Ser Arg
                485                 490                 495

Ala Ile Pro Val Ala Gly Ser Gly Asp Ser Ala Val Pro Ile Asn Ile
        500                 505                 510

Ala His Asn Glu Ser Asp Ser Gln Ala Phe Met Ser Arg Phe Gln Ser
    515                 520                 525

Glu Ile Ala Thr Ser Leu Thr Ala Ala Ala Ser Glu Leu Pro Cys
530                 535                 540

Thr Val Lys Leu Arg Val Trp Pro Tyr Asp Ile Lys Val Pro Cys Ala
545                 550                 555                 560

Leu Leu Asp Ala Glu Lys Cys Arg Leu Val Ile Pro His Ala Val Leu
                565                 570                 575

Cys Ser Glu Met Gly Ala His Phe Ser Pro Cys Gly Arg Phe Leu Ala
        580                 585                 590

Ala Cys Val Ala Cys Ile Ser Pro Ser Met Glu Ala Asp Pro Gly Phe
    595                 600                 605

His Gly Gln Phe Arg His Asp Ala Ala Thr Ser Pro Thr Arg His Pro
```

Ile Ala Ala His Pro Val Met Tyr Glu Leu Arg Ile Tyr Ser Leu Glu
625                 630                 635                 640

Glu Ala Asn Phe Gly Arg Val Leu Ala Ser Arg Leu Ile Arg Ala Ala
            645                 650                 655

His Cys Leu Thr Ser Ile Gln Phe Ser Pro Thr Ser Glu His Leu Leu
        660                 665                 670

Leu Ala Tyr Gly Arg Arg His Gly Ser Leu Leu Lys Ser Ile Val Ile
    675                 680                 685

Asp Gly Asp Thr Thr Leu Pro Val Tyr Thr Ile Leu Glu Val Tyr Arg
690                 695                 700

Val Ser Asp Met Glu Leu Val Arg Val Leu Pro Ser Ala Glu Asp Glu
705                 710                 715                 720

Val Asn Val Ala Cys Phe His Pro Leu Val Gly Gly Leu Val Tyr
                725                 730                 735

Gly Thr Lys Glu Gly Lys Leu Arg Ile Leu Gln Phe Asp Lys Ser Asn
            740                 745                 750

Gly Leu Asp Cys Thr Val Ser Cys Ser Pro Asp Glu Asp Met Leu Glu
    755                 760                 765

Val Pro Thr Tyr Ala Leu Glu Gly
770                 775

<210> SEQ ID NO 21
<211> LENGTH: 759
<212> TYPE: PRT
<213> ORGANISM: Artificial Sequence
<220> FEATURE:
<223> OTHER INFORMATION: the amino acid sequence of XP_015167963.1

<400> SEQUENCE: 21

Met Arg Ser Ser Met Ser Pro Asp Asn Ser Ser Ala Pro Ser Thr
1               5                   10                  15

Ser Arg Ser Ser Pro Pro Ser Ala Ala Ser Gln Asn Leu Asn Cys Lys
            20                  25                  30

His Ser Asn Val Phe Gln Leu Leu Thr Arg Arg Glu Val Ala Pro Arg
        35                  40                  45

Thr Lys Arg Ala Ser Arg Lys Phe Trp Gly Glu Asn Thr Lys Cys Thr
    50                  55                  60

Leu Asp Ser Tyr Gly Leu Lys Arg Gly Val Gly Ser Asp Ala Arg Gln
65                  70                  75                  80

Gly Leu Ile Ser Trp Val Glu Ala Glu Ser Leu Gln His Leu Ser Ala
                85                  90                  95

Lys Tyr Cys Ser Leu Leu Pro Pro Arg Ser Thr Ile Ala Ala Ala
            100                 105                 110

Phe Ser Pro Asp Gly Arg Thr Leu Ala Ser Thr His Gly Asp His Thr
        115                 120                 125

Val Lys Ile Ile Asp Cys Gln Thr Gly Lys Cys Leu Lys Val Met Ser
    130                 135                 140

Gly His Arg Arg Thr Pro Trp Val Val Arg Phe His Pro Leu Tyr Pro
145                 150                 155                 160

Glu Ile Leu Ala Ser Gly Ser Leu Asp His Glu Val Arg Leu Trp Asp
                165                 170                 175

Ala Lys Thr Ala Glu Cys Ile Gly Ser Arg Asp Phe Tyr Arg Pro Ile
            180                 185                 190

Ala Ser Ile Ala Phe His Ala Gln Gly Glu Val Leu Ala Val Ala Ser

```
            195                 200                 205
Gly His Lys Leu Tyr Ile Trp His Tyr Asn Arg Arg Gly Glu Ala Ser
210                 215                 220

Ser Pro Ala Ile Ile Leu Lys Thr Arg Arg Ser Leu Arg Ala Val His
225                 230                 235                 240

Phe His Pro His Gly Ala Pro Phe Leu Leu Thr Ala Glu Val Asn Asp
                    245                 250                 255

Leu Asp Ser Ser Asp Ser Ser Ile Thr Arg Ala Thr Ser Pro Gly Asn
                260                 265                 270

Leu Gln Tyr Pro Pro Pro Thr Val Tyr Leu Thr Asp Ala His Ser Thr
            275                 280                 285

Tyr Gln Ser Ala Ser Ala Asn Glu Leu Pro Ile Met Ser Gln Pro Phe
        290                 295                 300

Leu Ile Trp Pro Ser Ile Ala Arg Gly Asp Pro Arg Met Pro Met Gln
305                 310                 315                 320

Gln Ser Asp Thr Asp Val Gly Ser Asp Ser Ile Gln Gln Arg Ala Asp
                    325                 330                 335

Thr Ser Ser Ser Val Arg Leu Leu Thr Tyr Ser Thr Pro Ser Gly Gln
                340                 345                 350

Tyr Glu Leu Leu Leu Ser Pro Ile Glu Gln Ser Ala Ser Pro Thr Gln
            355                 360                 365

Glu Ala His Thr Ser Ser Val Arg Glu Asn Glu Thr Gly Asn Gln
        370                 375                 380

Pro Leu Val Asp Pro Met Glu Thr Asp Gly Gln Pro Glu Glu Arg Asn
385                 390                 395                 400

Asn Gln Phe Phe Pro Phe Ser Asp Pro Ala Tyr Trp Glu Leu Pro Phe
                    405                 410                 415

Leu Gln Gly Trp Leu Ile Gly Arg Ser Gln Ala Thr Arg Ser Glu Leu
                420                 425                 430

Ser Gly Ala Thr Ile Asn Pro Ser Thr Tyr Gly Glu Leu Glu Asn Pro
            435                 440                 445

Ser Ala Val Pro Leu Val Ile Ser Ser Asn Ser His Pro Arg Ser Gly
        450                 455                 460

Arg Ser Gly Ser Arg His Arg Ser Ser Arg Ser Arg Val Ile Pro Val
465                 470                 475                 480

Ala Gly Ala Gly Asp Gly Ala Ala Pro Val Asn Val Met His Asp Glu
                    485                 490                 495

Ser Asp Ser Gln Ile Ser Ile Gly Arg Ile Gln Ser Glu Ile Ala Thr
                500                 505                 510

Ser Leu Ala Ala Ala Ala Ala Glu Leu Pro Cys Thr Val Lys Leu
            515                 520                 525

Arg Ile Trp Pro Tyr Asp Ile Lys Val Pro Cys Ala Ala Leu Asp Ala
        530                 535                 540

Glu Arg Cys Arg Leu Ile Ile Pro His Ala Val Leu Cys Ser Glu Met
545                 550                 555                 560

Gly Ala His Phe Ser Pro Cys Gly Arg Phe Leu Ala Ala Cys Val Ala
                    565                 570                 575

Cys Ile Leu Pro Asn Leu Asp Ser Asp Pro Gly Phe His Gly His Leu
                580                 585                 590

His His Asp Thr Met Ala Ala Ala Thr Ser Pro Thr Arg His Pro Val
            595                 600                 605

Ala Ala His Gln Val Met Tyr Glu Leu Arg Ile Tyr Ser Leu Glu Glu
        610                 615                 620
```

Glu Thr Phe Gly Ser Val Leu Ala Ala Arg Ala Ile Arg Ala Ala His
625                 630                 635                 640

Cys Leu Thr Ser Ile Gln Phe Ser Pro Thr Ser Glu His Leu Leu Leu
        645                 650                 655

Ala Tyr Gly Arg Arg His Ser Ser Leu Leu Lys Ser Val Val Ile Asp
            660                 665                 670

Gly Asp Thr Thr Ile Pro Ile Tyr Thr Ile Leu Glu Val Tyr Arg Val
                675                 680                 685

Ser Asp Met Glu Leu Val Arg Val Leu Pro Ser Thr Glu Asp Glu Val
690                 695                 700

Asn Val Ala Cys Phe His Pro Ser Val Gly Gly Leu Val Tyr Gly
705                 710                 715                 720

Thr Lys Glu Gly Lys Leu Arg Ile Leu Gln Tyr Asp Asn Ser Asn Cys
                725                 730                 735

Leu Gly Arg Thr Ile Ser Cys Ser Pro Val Glu Asn Met Leu Glu Val
            740                 745                 750

Pro Thr Tyr Ala Leu Glu Gly
        755

<210> SEQ ID NO 22
<211> LENGTH: 736
<212> TYPE: PRT
<213> ORGANISM: Artificial Sequence
<220> FEATURE:
<223> OTHER INFORMATION: the amino acid sequence of XP_015167964.1

<400> SEQUENCE: 22

Met Arg Ser Ser Met Ser Pro Asp Asn Ser Ser Ala Pro Ser Thr
1               5                   10                  15

Ser Arg Ser Ser Pro Pro Ser Ala Ala Ser Gln Asn Leu Asn Cys Lys
            20                  25                  30

His Ser Asn Val Phe Gln Leu Leu Thr Arg Arg Glu Val Ala Pro Arg
        35                  40                  45

Thr Lys Arg Ala Ser Arg Lys Phe Trp Gly Glu Asn Thr Lys Cys Thr
50                  55                  60

Leu Asp Ser Tyr Gly Leu Lys Arg Gly Val Gly Ser Asp Ala Arg Gln
65                  70                  75                  80

Gly Leu Ile Ser Trp Val Glu Ala Glu Ser Leu Gln His Leu Ser Ala
                85                  90                  95

Lys Tyr Cys Ser Leu Leu Pro Pro Arg Ser Thr Ile Ala Ala Ala
            100                 105                 110

Phe Ser Pro Asp Gly Arg Thr Leu Ala Ser Thr His Gly Asp His Thr
        115                 120                 125

Val Lys Ile Ile Asp Cys Gln Thr Gly Lys Cys Leu Lys Val Met Ser
    130                 135                 140

Gly His Arg Arg Thr Pro Trp Val Val Arg Phe His Pro Leu Tyr Pro
145                 150                 155                 160

Glu Ile Leu Ala Ser Gly Ser Leu Asp His Glu Val Arg Leu Trp Asp
                165                 170                 175

Ala Lys Thr Ala Glu Cys Ile Gly Ser Arg Asp Phe Tyr Arg Pro Ile
            180                 185                 190

Ala Ser Ile Ala Phe His Ala Gln Gly Glu Val Leu Ala Val Ala Ser
        195                 200                 205

Gly His Lys Leu Tyr Ile Trp His Tyr Asn Arg Arg Gly Glu Ala Ser
    210                 215                 220

```
Ser Pro Ala Ile Ile Leu Lys Thr Arg Arg Ser Leu Arg Ala Val His
225                 230                 235                 240

Phe His Pro His Gly Ala Pro Phe Leu Leu Thr Ala Glu Val Asn Asp
            245                 250                 255

Leu Asp Ser Ser Asp Ser Ser Ile Thr Arg Ala Thr Ser Pro Ala Asn
                260                 265                 270

Glu Leu Pro Ile Met Ser Gln Pro Phe Leu Ile Trp Pro Ser Ile Ala
            275                 280                 285

Arg Gly Asp Pro Arg Met Pro Met Gln Gln Ser Asp Thr Asp Val Gly
            290                 295                 300

Ser Asp Ser Ile Gln Gln Arg Ala Asp Thr Ser Ser Val Arg Leu
305                 310                 315                 320

Leu Thr Tyr Ser Thr Pro Ser Gly Gln Tyr Glu Leu Leu Ser Pro
                325                 330                 335

Ile Glu Gln Ser Ala Ser Pro Thr Gln Glu Ala His Thr Ser Ser Ser
                340                 345                 350

Val Arg Glu Asn Glu Thr Gly Asn Gln Pro Leu Val Asp Pro Met Glu
            355                 360                 365

Thr Asp Gly Gln Pro Glu Glu Arg Asn Asn Gln Phe Phe Pro Phe Ser
370                 375                 380

Asp Pro Ala Tyr Trp Glu Leu Pro Phe Leu Gln Gly Trp Leu Ile Gly
385                 390                 395                 400

Arg Ser Gln Ala Thr Arg Ser Glu Leu Ser Gly Ala Thr Ile Asn Pro
                405                 410                 415

Ser Thr Tyr Gly Glu Leu Glu Asn Pro Ser Ala Val Pro Leu Val Ile
            420                 425                 430

Ser Ser Asn Ser His Pro Arg Ser Gly Arg Ser Gly Ser Arg His Arg
            435                 440                 445

Ser Ser Arg Ser Arg Val Ile Pro Val Ala Gly Ala Gly Asp Gly Ala
450                 455                 460

Ala Pro Val Asn Val Met His Asp Glu Ser Asp Ser Gln Ile Ser Ile
465                 470                 475                 480

Gly Arg Ile Gln Ser Glu Ile Ala Thr Ser Leu Ala Ala Ala Ala
                485                 490                 495

Ala Glu Leu Pro Cys Thr Val Lys Leu Arg Ile Trp Pro Tyr Asp Ile
            500                 505                 510

Lys Val Pro Cys Ala Ala Leu Asp Ala Glu Arg Cys Arg Leu Ile Ile
            515                 520                 525

Pro His Ala Val Leu Cys Ser Glu Met Gly Ala His Phe Ser Pro Cys
            530                 535                 540

Gly Arg Phe Leu Ala Ala Cys Val Ala Cys Ile Leu Pro Asn Leu Asp
545                 550                 555                 560

Ser Asp Pro Gly Phe His Gly His Leu His His Asp Thr Met Ala Ala
                565                 570                 575

Ala Thr Ser Pro Thr Arg His Pro Val Ala His Gln Val Met Tyr
            580                 585                 590

Glu Leu Arg Ile Tyr Ser Leu Glu Glu Glu Thr Phe Gly Ser Val Leu
            595                 600                 605

Ala Ala Arg Ala Ile Arg Ala Ala His Cys Leu Thr Ser Ile Gln Phe
            610                 615                 620

Ser Pro Thr Ser Glu His Leu Leu Leu Ala Tyr Gly Arg Arg His Ser
625                 630                 635                 640
```

-continued

```
Ser Leu Leu Lys Ser Val Val Ile Asp Gly Asp Thr Thr Ile Pro Ile
            645                 650                 655

Tyr Thr Ile Leu Glu Val Tyr Arg Val Ser Asp Met Glu Leu Val Arg
            660                 665                 670

Val Leu Pro Ser Thr Glu Asp Glu Val Asn Val Ala Cys Phe His Pro
            675                 680                 685

Ser Val Gly Gly Leu Val Tyr Gly Thr Lys Glu Gly Lys Leu Arg
    690             695             700

Ile Leu Gln Tyr Asp Asn Ser Asn Cys Leu Gly Arg Thr Ile Ser Cys
705             710                 715                 720

Ser Pro Val Glu Asn Met Leu Glu Val Pro Thr Tyr Ala Leu Glu Gly
            725                 730                 735
```